United States Patent
Nakao et al.

(10) Patent No.: US 11,926,581 B2
(45) Date of Patent: Mar. 12, 2024

(54) SULFONIUM SALT, PHOTOACID GENERATOR, CURABLE COMPOSITION, AND RESIST COMPOSITION

(71) Applicant: SAN-APRO LTD., Kyoto (JP)

(72) Inventors: Takuto Nakao, Kyoto (JP); Yusaku Takashima, Kyoto (JP)

(73) Assignee: SAN-APRO LIMITED, Kyoto (JP)

( * ) Notice: Subject to any disclaimer, the term of this patent is extended or adjusted under 35 U.S.C. 154(b) by 820 days.

(21) Appl. No.: 17/047,446

(22) PCT Filed: Apr. 9, 2019

(86) PCT No.: PCT/JP2019/015390
§ 371 (c)(1),
(2) Date: Oct. 14, 2020

(87) PCT Pub. No.: WO2019/225185
PCT Pub. Date: Nov. 28, 2019

(65) Prior Publication Data
US 2021/0147352 A1   May 20, 2021

(30) Foreign Application Priority Data
May 25, 2018 (JP) .................. 2018-100323

(51) Int. Cl.
| C07C 381/12 | (2006.01) |
| G03F 7/038 | (2006.01) |
| G03F 7/09 | (2006.01) |
| G03F 7/20 | (2006.01) |

(52) U.S. Cl.
CPC .......... *C07C 381/12* (2013.01); *G03F 7/0382* (2013.01); *G03F 7/094* (2013.01); *G03F 7/2002* (2013.01); *G03F 7/2039* (2013.01)

(58) Field of Classification Search
CPC .............. C07C 381/12; C07C 2602/42; C07C 2603/18; C07C 309/04; C07C 309/06; C07C 309/19; C07C 309/30; G03F 7/0382; G03F 7/094; G03F 7/2002; G03F 7/2039; G03F 7/0045; G03F 7/038; G03F 7/039; C07F 5/00; C07F 5/02; C07F 9/28; C08F 4/32; C08G 59/68; C09K 3/00
USPC .................. 430/270.1, 271.1, 272.1, 311
See application file for complete search history.

(56) References Cited

U.S. PATENT DOCUMENTS

| 2008/0045621 A1 | 2/2008 | Ito et al. |
| 2011/0300482 A1 | 12/2011 | Suzuki et al. |

FOREIGN PATENT DOCUMENTS

| JP | 50-151997 A | 12/1975 |
| JP | 2-178303 A | 7/1990 |
| JP | 9-118663 A | 5/1997 |
| JP | 2000-66385 A | 3/2000 |
| JP | 2008-77057 A | 4/2008 |
| JP | 2010-215616 A | 9/2010 |
| JP | 2019-73470 A | 5/2019 |
| WO | 2008-117619 A1 | 10/2008 |
| WO | 2017-212963 A1 | 12/2017 |

OTHER PUBLICATIONS

JP 2011-195499; Suzuki Oct. 6, 2011.*
WO 2014-061062; Ikeda Apr. 24, 2014.*
International Search Report dated Jul. 9, 2019, issued in counterpart application No. PCT/JP2019/015390 (2 pages).
O'Brien et al., "Mid-UV photoresists combining chemical amplification and dissolution inhibition", SPIE, Advances in Resist Technology and Processing V, 1998, vol. 920, pp. 42-50, cited in Specification (9 pages).
Ito, "Aqueous base developable deep UV resist systems based on novel monomeric and polymeric dissolution inhibitors", SPIE, Advances in Resist Technology and Processing V, 1988, vol. 920, pp. 33-41, cited in Specification (9 pages).

\* cited by examiner

*Primary Examiner* — Caleen O Sullivan
(74) *Attorney, Agent, or Firm* — WHDA, LLP

(57) ABSTRACT

The sulfonium salt has high photosensitivity to i-rays and high compatibility with cationically polymerizable compounds such as epoxy compounds, and is excellent storage stability in formulations containing such compounds. The sulfonium salt is represented by general formula (1). In formula (1), R represents an alkyl group or an aryl group; substituents, R1 to R5, each independently represent an alkyl group, a hydroxy group, an alkoxy group, an aryl group, an aryloxy group, a hydroxy(poly)alkyleneoxy group, or a halogen atom; R6 to R9 each independently represent an alkyl group, an aryl group, or a hydrogen atom; $m^1$ to $m^5$ each represent the number of occurrences of each of R1 to R5, $m^1$ and $m^4$ represent an integer of 0 to 3, $m^2$ and $m^5$ represent an integer of 0 to 4, $m^3$ represents an integer of 0 to 5, and $X^-$ represents a monovalent polyatomic anion.

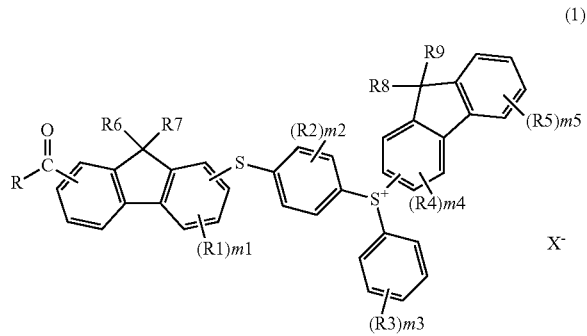

(1)

17 Claims, No Drawings

SULFONIUM SALT, PHOTOACID GENERATOR, CURABLE COMPOSITION, AND RESIST COMPOSITION

TECHNICAL FIELD

The present invention relates firstly to a sulfonium salt and secondly to a photoacid generator, more specifically, a photo-acid generator containing a specific sulfonium salt suitable for curing a cationically polymerizable compound by the action of an active energy ray such as light, an electron beam, or an X-ray.

The present invention relates thirdly to a curable composition containing the photoacid generator and a cured product obtained by curing the same.

The present invention relates fourthly to a chemically amplified positive photoresist composition containing the photoacid generator and a method for forming a resist pattern using the composition.

The present invention relates fifthly to a chemically amplified negative photoresist composition containing the photoacid generator and a cured product obtained by curing the same.

BACKGROUND ART

A photoacid generator is a generic name for a compound which decomposes and generates an acid by application of heat or an active energy ray such as an electron beam, or an X-ray, and is used for several reactions such as polymerization, crosslinking reaction and deprotection reaction as an active species, an acid generated by application of an active energy ray.

Specific examples of these reactions include a polymerization of a cationic polymerizable compound, a crosslinking reaction of a phenol resin under crosslinking agent, and a deprotection reaction of polymer having an alkali-soluble resin as a protecting group.

Recently, manufacture of electric parts and formation of semiconductor elements are being done actively by making full use of photolithographic technology using photoresists, and i-line with a wavelength of 365 nm is widely used as an active energy ray for the manufacture of various precision parts such as semiconductor packages. Some reasons for this are that medium- or high-pressure mercury lamps, which are available as irradiation light sources at a low cost and have high emission intensity, can be used.

Also, medium- or high-pressure mercury lamps can be used most commonly in the field of paints, adhesives, and coatings other than photolithography and LED lamps having an emission wavelength in the i-line region (360 nm to 390 nm) are currently becoming widespread. It is therefore considered that a need for photo-acid generators having high sensitivity to the i-line will further increase in the future.

However, some existing photo-acid generators such as triarylsulfonium salts (Patent Document 1), phenacylsulfonium salts having a naphthalene skeleton (Patent Document 2), and dialkylbenzylsulfonium salts (Patent Document 3) have low sensitivity to the i-line and therefore need to be used in combination with a sensitizer so that the sensitivity can be increased. The present inventors have proposed triarylsulfonium salts having high sensitivity to the i-line (Patent Document 4). However, these salts have not enough sensitivity to the i-line.

Also, in recent years, as the size of electronic devices has further decreased, high-density packaging of semiconductor packages has progressed, in which the packaging density has been increased based on multi-pin thin film packaging or package downsizing, or two- or three-dimensional packaging techniques using flip-chip method. Materials for use in such high-precision photo-fabrication include positive photosensitive resin compositions containing an oxime sulfonate compound (Patent Document 5, Non-Patent Document 1 and 2). When this composition is irradiated with (exposed to) radiations, an acid is generated from the photoacid generator, and heat treatment after the exposure facilitates the diffusion of the acid and the acid-catalyzed reaction, so that the base resin in the resin composition undergoes a change in solubility in an alkali. Such a composition is called a positive photoresist, because the base resin, which is insoluble in alkali before the exposure, is made alkali-soluble. However, this positive photoresist composition has low storage stability because of containing an oxime sulfonate compound, and therefore needs complicated storage-temperature control and has a practical problem.

Moreover, there are proposed photosensitive resin compositions using an alkali-soluble resin having a phenolic hydroxyl group and a triazine-type photoacid generator as surface protecting films, interlayer dielectric films, and others for use in semiconductor devices in electronics (Patent Documents 6 and 7). Such a composition is called a negative photoresist, in which an acid is generated from a photoacid generator by exposure to light and facilitates the reaction between a crosslinking agent and an alkali-soluble resin so that the resin becomes insoluble in a developing solution. However, such triazine-type photoacid generator have a problem that the photoacid generator is hydrochloric or hydrobromic acid, which is volatile and pollutes facilities.

PRIOR ART DOCUMENTS

Patent Documents

Patent Document 1: Japanese Patent Application Laid-Open (JP-A) No. 50-151997
Patent Document 2: JP-A No. 09-118663
Patent Document 3: JP-A No. 02-178303
Patent Document 4: JP-A No. 2010-215616
Patent Document 5: JP-A No. 2000-66385
Patent Document 6: JP-A No. 2008-77057
Patent Document 7: WO2008-117619

Non-Patent Documents

Non-Patent Document 1: M. J. O'Brien, J. V. Crivello, SPIE Vol. 920, Advances in Resist Technology and Processing, p. 42 (1988)
Non-Patent Document 2: H. ITO, SPIE Vol. 920, Advances in Resist Technology and Processing, p. 33 (1988)

SUMMARY OF THE INVENTION

Problems to be Solved by the Invention

Under the above circumstances, a first object of the invention is to provide a new sulfonium salt having high photosensitivity to the i-line.

A second object of the invention is to provide a new photoacid generator that comprises a sulfonium salt and has high photosensitivity to the i-line and high compatibility with a cationically polymerizable compound such as an epoxy compound, and also has excellent storage stability when formulated with a cationically polymerizable compound such as an epoxy compound.

A third object of the invention is to provide an energy ray-curable composition and a cured product each produced with the above photoacid generator.

A fourth object of the invention is to provide a chemically amplified positive photoresist composition produced with the above photoacid generator, and a method for the composition.

A fifth object of the invention is to provide a chemically amplified negative photoresist composition and a cured product each produced with the above photoacid generator.

Means for Solving the Problems

The inventors have found that a sulfonium salt represented by formula (1) described below is suitable for achieving the above objects. Thus, the invention provides a sulfonium salt represented by formula (1).

[Chemical Formula 1]

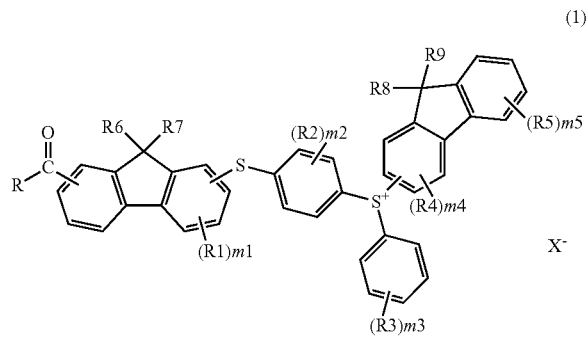

(1)

[in formula (1), R represents an alkyl group or an aryl group; substituents, R1 to R5, each independently represent an alkyl group, a hydroxy group, an alkoxy group, an aryl group, an aryloxy group, a hydroxy(poly)alkyleneoxy group, or a halogen atom; R6 to R9 each independently represent an alkyl group, an aryl group, or a hydrogen atom; $m^1$ to $m^5$ each represent the number of occurrences of each of R1 to R5, $m^1$ and $m^4$ represent an integer of 0 to 3, $m^2$ and $m^5$ represent an integer of 0 to 4, $m^3$ represents an integer of 0 to 5, and $X^-$ represents a monovalent polyatomic anion]

The invention also provides a photoacid generator comprising the above sulfonium salt.

The invention also provides an energy ray-curable composition, comprising the above photoacid generator and a cationically polymerizable compound.

The invention further provides a cured product obtained by curing the above energy ray-curable composition.

The invention further provides a chemically amplified positive photoresist composition comprising the above photoacid generator and a resin ingredient (B) increasing its solubility in an alkali under the action of an acid.

The invention further provides a method for forming a resist pattern, comprising: a lamination step of laminating a photoresist layer with a thickness of 5 to 150 μm comprising anyone of the above chemically amplified positive photoresist compositions to obtain a photoresist laminate; an exposure step of site-selectively irradiating the photoresist laminate with light or a radiation; and a development step of developing the photoresist laminate after the exposure step to obtain a resist pattern.

The invention further provides a chemically amplified negative photoresist composition comprising: the above photoacid generator; an ingredient (F) that is an alkali-soluble resin having a phenolic hydroxyl group; and a crosslinking agent ingredient (G).

The invention further provides a cured product obtained by curing any one of the above chemically amplified negative photoresist compositions.

Effects of the Invention

The sulfonium salt of the invention has excellent photosensitivity to active energy rays such as visible light, ultraviolet rays, electron beams, and X-rays, and high compatibility with a cationically polymerizable compound such as an epoxy compound, and also has excellent storage stability when formulated with a cationically polymerizable compound such as an epoxy compound.

The photoacid generator of the invention has excellent curing properties under the action of ultraviolet light, particularly, i-line, when used to cure a cationically polymerizable compound, and makes it possible to cure a cationically polymerizable compound with no sensitizer. The photoacid generator of the invention also has excellent thick-film-curing properties.

The energy ray-curable composition of the invention contains the above photoacid generator and therefore can be cured with ultraviolet light. The energy ray-curable composition of the invention also has high storage stability and excellent cost effectiveness and workability, because no sensitizer needs to be used.

The cured product of the invention can be obtained with no sensitizer and therefore is free from the problem of discoloration or deterioration, which would be caused by any residual sensitizer.

The chemically amplified positive photoresist composition and the chemically amplified negative photoresist composition of the invention each contain the above photoacid generator and therefore can form a resist with high sensitivity to the i-line, in other words, it is possible to form pattern by low exposure compared with conventional compositions. The chemically amplified positive photoresist composition and the chemically amplified negative photoresist composition of the invention also have high storage stability and can form a good resist pattern shape.

MODE FOR CARRYING OUT THE INVENTION

Hereinafter, embodiments of the invention are described in detail.

A sulfonium salt of the present invention is represented by formula (1).

[Chemical Formula 2]

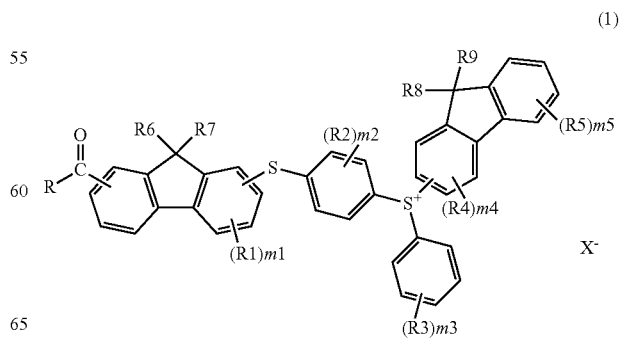

(1)

[in formula (1), R represents an alkyl group or an aryl group; substituents, R1 to R5, each independently represent an alkyl group, a hydroxy group, an alkoxy group, an aryl group, an aryloxy group, a hydroxy(poly)alkyleneoxy group, or a halogen atom; R6 to R9 each independently represent an alkyl group, an aryl group, or a hydrogen atom; $m^1$ to $m^5$ each represent the number of occurrences of each of R1 to R5, $m^1$ and $m^4$ represent an integer of 0 to 3, $m^2$ and $m^5$ represent an integer of 0 to 4, $m^3$ represents an integer of 0 to 5, and $X^-$ represents a monovalent polyatomic anion]

In formula (1), examples of the alkyl group for R include straight chain alkyl groups having 1 to 18 carbon atoms (such as methyl, ethyl, n-propyl, n-butyl, n-pentyl, n-octyl, n-decyl, n-dodecyl, n-tetradecyl, n-hexadecyl, and n-octadecyl), branched chain alkyl groups having 1 to 18 carbon atoms (such as isopropyl, isobutyl, sec-butyl, tert-butyl, isopentyl, neopentyl, tert-pentyl, isohexyl, and isooctadecyl), and cycloalkyl groups having 3 to 18 carbon atoms (such as cyclopropyl, cyclobutyl, cyclopentyl, cyclohexyl, and 4-decylcyclohexyl).

In formula (1), examples of the aryl group for R include aryl groups having 6 to 12 carbon atoms (such as phenyl, tolyl, dimethylphenyl, naphthyl and biphenylyl).

In formula (1), examples of the alkyl group for $R^1$ to $R^9$ include straight chain alkyl groups having 1 to 18 carbon atoms (such as methyl, ethyl, n-propyl, n-butyl, n-pentyl, n-octyl, n-decyl, n-dodecyl, n-tetradecyl, n-hexadecyl, and n-octadecyl), branched chain alkyl groups having 1 to 18 carbon atoms (such as isopropyl, isobutyl, sec-butyl, tert-butyl, isopentyl, neopentyl, tert-pentyl, isohexyl, and isooctadecyl), and cycloalkyl groups having 3 to 18 carbon atoms (such as cyclopropyl, cyclobutyl, cyclopentyl, cyclohexyl, and 4-decylcyclohexyl).

In formula (1), examples of the alkoxy group for $R^1$ to $R^5$ include straight or branched chain alkoxy groups having 1 to 18 carbon atoms (such as methoxy, ethoxy, propoxy, isopropoxy, butoxy, isobutoxy, sec-butoxy, tert-butoxy, hexyloxy, decyloxy, dodecyloxy, and octadecyloxy).

In formula (1), examples of the aryl group for $R^1$ to $R^9$ include aryl groups having 6 to 12 carbon atoms (such as phenyl, tolyl, dimethylphenyl, naphthyl and biphenylyl).

In formula (1), examples of the aryloxy group for $R^1$ to $R^5$ include aryloxy groups having 6 to 10 carbon atoms (such as phenoxy and naphthyloxy).

In formula (1), examples of the hydroxy(poly)alkyleneoxy group for $R^1$ to $R^5$ include hydroxy(poly)alkyleneoxy groups represented by formula (2):

$$HO(-AO)q- \qquad (2)$$

[wherein AO represents an ethyleneoxy group and/or a propyleneoxy group, and q represents an integer of 1 to 5].

In formula (1), examples of the halogen atom for $R^1$ to $R^5$ include a fluorine atom, a chlorine atom, a bromine atom, and an iodine atom.

In formula (1), $R^1$ to $R^9$ are independent of one another and therefore may be the same as or different from one another.

R preferably represents alkyl groups having 1 to 4 carbon atoms or aryl groups having 6 to 12 carbon atoms, more preferably represents a methyl group, a butyl group, a phenyl group, a naphthyl group, or biphenylyl group, and in particular, preferably represents a methyl group, or a phenyl group from the viewpoint of availability of industrial raw materials.

$R^1$ to $R^5$ each preferably represent alkyl group, alkoxy group, aryloxy group, or halogen atom, and in particular, preferably represent a methyl group, or a methoxy group.

$R^6$ to $R^9$ each preferably represent alkyl group, or aryl group, and in particular, preferably represent a methyl group, or a phenyl group from the viewpoint of availability of industrial raw materials.

In formula (1), $m^1$ to $m^5$ each represent the number of occurrences of each of R1 to R5, $m^1$ and $m^4$ represent an integer of 0 to 3, $m^2$ and $m^5$ represent an integer of 0 to 4, $m^3$ represents an integer of 0 to 5, $m^1$ to $m^5$ each preferably represent an integer of 0 to 2, more preferably represent 0.

Among formula (1), the sulfonium salts having a methyl group as $R^6$ to $R^9$ each, and 0 as $m^1$ to $m^5$ each are preferred.

Preferred specific examples are shown below.

[Chemical Formula 3]

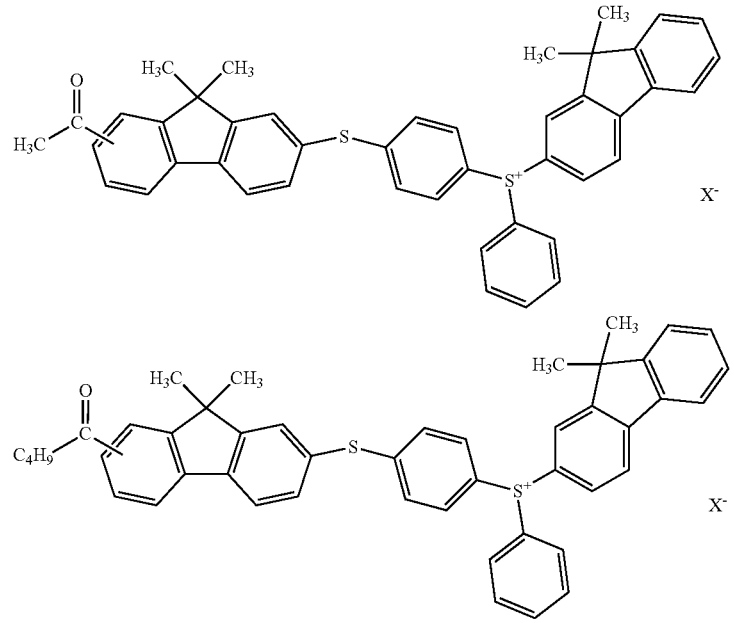

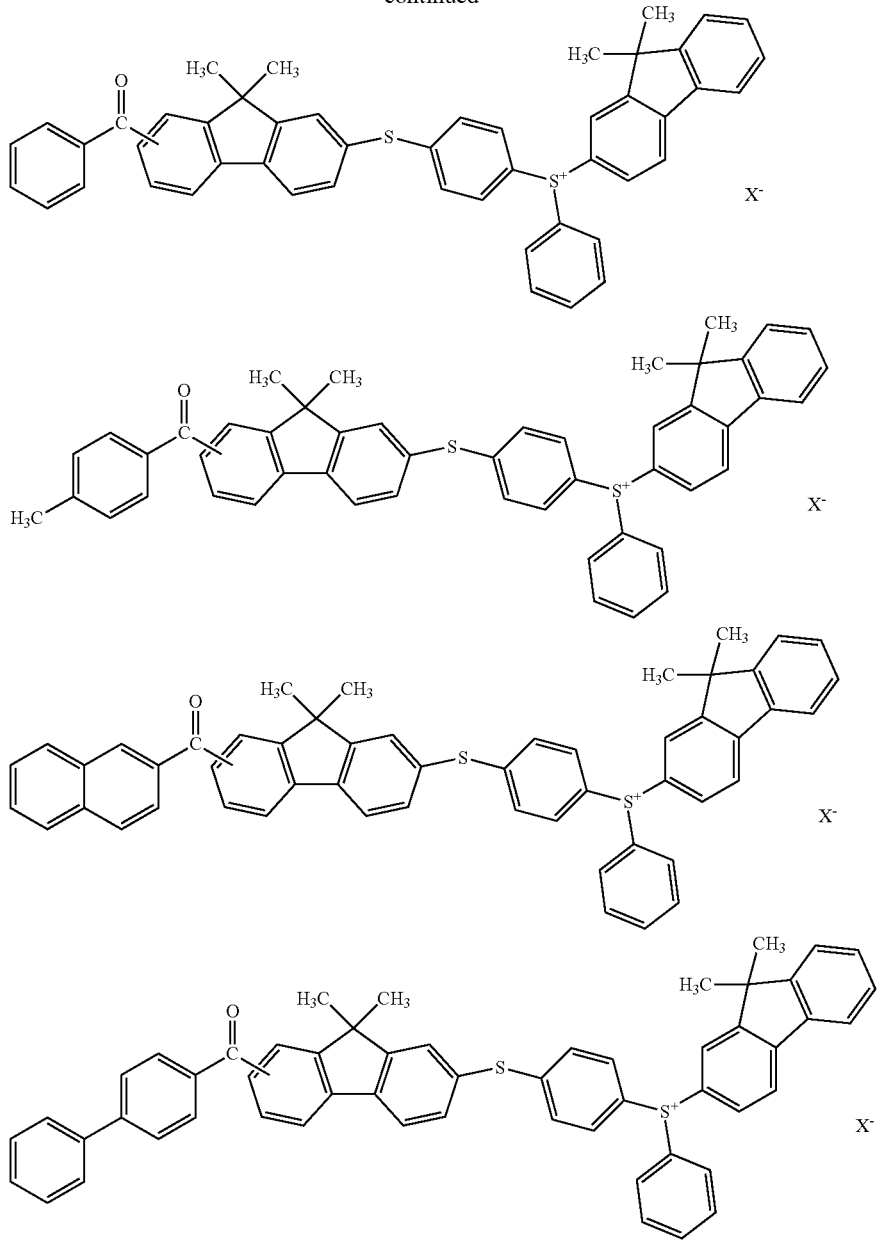

In formula (1), X⁻ represents an anion corresponding to an acid (HX) which is produced by irradiating the sulfonium salt of the invention with an active energy ray (such as visible light, an ultraviolet ray, an electron beam, or an X-ray). X⁻ is not restricted, as long as it represents a monovalent polyatomic anion. X⁻ preferably represents an anion represented by $MY_a^-$, $(Rf))_bPF_{6-b}^-$, $R^{10}_cBY_{4-c}^-$, $R^{10}_cGaY_{4-c}^-$, $R^{11}SO_3^-$, $(R^{11}SO_2)_3C^-$, or $(R^{11}SO_2)_2N^-$.

M represents a phosphorus atom, a boron atom, or an antimony atom.

Y represents a halogen atom (preferably a fluorine atom).

Rf represents an alkyl group (preferably an alkyl group having 1 to 8 carbon atoms) whose 80% by mole or more of hydrogen atoms are substituted with fluorine atoms. Examples of the alkyl group to be substituted with fluorine for Rf include straight chain alkyl groups (such as methyl, ethyl, propyl, butyl, pentyl, and octyl), branched alkyl groups (such as isopropyl, isobutyl, sec-butyl, and tert-butyl), and cycloalkyl groups (such as cyclopropyl, cyclobutyl, cyclopentyl, and cyclohexyl). The ratio at which the hydrogen atoms of these alkyl groups are substituted with fluorine atoms in Rf is preferably 80% by mole or more, more preferably 90% by mole or more, in particular, preferably 100% by mole, based on the molar number of the hydrogen atoms in the original alkyl group. When the fluorine atom substitution ratio is in the preferred ranges, the sulfonium salt will have higher photosensitivity. In particular, preferred examples of Rf include CF₃—, CF₃CF₂—, (CF₃)₂CF—, CF₃CF₂CF₂—, CF₃CF₂CF₂CF₂—, (CF₃)₂CFCF₂—, CF₃CF₂(CF₃)CF—, and (CF₃)₃C—. The number of occurrences b of Rf are independent of one another and therefore may be the same as or different from one another.

P represents a phosphorus atom, and F represents a fluorine atom.

$R^{10}$ represents a phenyl group whose hydrogen atoms are partially substituted with at least one element or electron-withdrawing group. For example, such one element includes a halogen atom, examples of which include a fluorine atom, a chlorine atom, and a bromine atom. Examples of the electron-withdrawing group include a trifluoromethyl group, a nitro group, and a cyano group. Among them, preferred is a phenyl group one of whose hydrogen atoms is substituted with a fluorine atom or a trifluoromethyl group. The number of occurrences c of $R^{10}$ groups are independent of one another and therefore may be the same as or different from one another.

B represents a boron atom, and Ga represents a gallium atom.

$R^{11}$ represents an alkyl group having 1 to 20 carbon atoms, a perfluoroalkyl group having 1 to 20 carbon atoms, or an aryl group having 6 to 20 carbon atoms, wherein the alkyl group and the perfluoroalkyl group may each be any of a straight chain, a branched chain, or a cyclic group, and the aryl group may be substituted or unsubstituted.

S represents a sulfur atom, O represents an oxygen atom, C represents a carbon atom, and N represents a nitrogen atom.

a represents an integer of 4 to 6.

b preferably represents an integer of 1 to 5, more preferably 2 to 4, in particular, preferably 2 or 3.

c preferably represents an integer of 1 to 4, more preferably 4.

Examples of the anion represented by $MY_a^-$ include anions represented by $SbF_6^-$, $PF_6^-$, and $BF_4^-$.

Examples of the anion represented by $(Rf)_b PF_{6-b}^-$ include anions represented by $(CF_3CF_2)_2PF_4^-$ $(CF_3CF_2)_3PF_3^-$ $(CF_3)_2CF)_2PF_4^-$ $(CF_3)_2CF)_3PF_3^-$ $(CF_3CF_2CF_2)_2PF_4^-$ $(CF_3CF_2CF_2)_3PF_3^-$ $(CF_3)_2CFCF_2)_2PF_4^-$ $((CF_3)_2CFCF_2)_3PF_3^-$, $(CF_3CF_2CF_2CF_2)_2PF_4^-$, and $(CF_3CF_2CF_2CF_2)_3PF_3^-$. Among them, preferred are anions represented by $(CF_3CF_2)_3PF_3^-$, $(CF_3CF_2CF_2)_3PF_3^-$ $((CF_3)_2CF)_3PF_3^-$ $((CF_3)_2CF)_2PF_4^-$ $((CF_3)_2CFCF_2)_3PF_3^-$, and $((CF_3)_2CFCF_2)_2PF_4^-$.

Examples of the anion represented by $R^{10}{}_c BY_{4-c}^-$ include anions represented by $(C_6F_5)_4B^-$, $((CF_3)_2C_6H_3)_4B^-$, $(CF_3C_6H_4)_4B^-$, $(C_6F_5)_2BF_2^-$, $C_6F_5BF_3^-$, and $(C_6H_3F_2)_4B^-$. Among them, preferred are anions represented by $(C_6F_5)_4B^-$ and $((CF_3)_2C_6H_3)_4B^-$.

Examples of the anion represented by $R^{10}{}_c GaY_{4-c}^-$ include anions represented by $(C_6F_5)_4Ga^-$, $((CF_3)_2C_6H_3)_4Ga^-$, $(CF_3C_6H_4)_4Ga^-$, $(C_6F_5)_2GaF_2^-$, $C_6F_5GaF_3^-$, and $(C_6H_3F_2)_4Ga^-$. Among them, preferred are anions represented by $(C_6F_5)_4Ga^-$ and $((CF_3)_2C_6H_3)_4Ga^-$.

Examples of the anion represented by $R^{11}SO_3^-$ include trifluoromethanesulfonate anion, pentafluoroethanesulfonate anion, heptafluoropropanesulfonate anion, nonafluorobutanesulfonate anion, pentafluorophenylsulfonate anion, p-toluenesulfonate anion, benzenesulfonate anion, camphorsulfonate anion, methanesulfonate anion, ethanesulfonate anion, propanesulfonate anion, and butanesulfonate anion. Among them, preferred are trifluoromethanesulfonate anion, nonafluorobutanesulfonate anion, methanesulfonate anion, butanesulfonate anion, camphorsulfonate anion, benzenesulfonate anion, and p-toluenesulfonate anion.

Examples of the anion represented by $(R^{11}SO_2)_3C^-$ include anions represented by $(CF_3SO_2)_3C^-$, $(C_2F_5SO_2)_3C^-$, $(C_3F_7SO_2)_3C^-$, and $(C_4F_9SO_2)_3C^-$.

Examples of the anion represented by $(R^{11}SO_2)_2N^-$ include anions represented by $(CF_3SO_2)_2N^-$, $(C_2F_5SO_2)_2N^-$, $(C_3F_7SO_2)_2N^-$, and $(C_4F_9SO_2)_2N^-$.

Examples of the monovalent polyatomic anion that may be used include not only anions represented by $MY_a^-$, $(Rf)_b PF_{6-b}^-$, $R^{10}{}_c BY_{4-c}^-$, $R^{10}{}_c GaY_{4-c}^-$, $R^{11}SO_3^-$, $(R^{11}SO_2)_3C^-$, or $(R^{11}SO_2)_2N^-$ but also perhalogenate ions (such as $ClO_4^-$ and $BrO_4^-$), halogenated sulfonate ions (such as $FSO_3^-$ and $ClSO_3^-$), sulfate ions (such as $CH_3SO_4^-$, $CF_3SO_4^-$, and $HSO_4^-$), carbonate ions (such as $HCO_3^-$ and $CH_3CO_3^-$), aluminate ions (such as $AlCl_4^-$ and $AlF_4^-$), hexafluoro bismuthate ion ($BiF_6^-$), carboxylate ions (such as $CH_3COO^-$, $CF_3COO^-$, $C_6H_5COO^-$, $CH_3C_6H_4COO^-$, $C_6F_5COO^-$, and $CF_3C_6H_4COO^-$) arylborate ions (such as $B(C_6H_5)_4^-$ and $CH_3CH_2CH_2CH_2B(C_6H_5)_3^-$), thiocyanate ion ($SCN^-$), and nitrate ion ($NO_3^-$).

Among these $X^-$, $X^-$ preferably represents anions represented by $MY_a^-$, $(Rf)_b PF_{6-b}^-$, $R^{10}{}_c BY_{4-c}^-$, $R^{10}{}_c GaY_{4-c}^-$, $R^{11}SO_3^-$, $(R^{11}SO_2)_3C^-$, and $(R^{11}SO_2)_2N^-$, more preferably represents $SbF_6^-$, $PF_6^-$, $(CF_3CF_2)_3PF_3^-$, $(C_6F_5)_4B^-$, $((CF_3)_2C_6H_3)_4B^-$, $(C_6F_5)_4Ga^-$, $((CF_3)_2C_6H_3)_4Ga^-$, trifluoromethanesulfonate anion, nonafluorobutanesulfonate anion, methanesulfonate anion, butanesulfonate anion, camphorsulfonate anion, benzenesulfonate anion, p-toluenesulfonate anion, $(CF_3SO_2)_3C^-$ and $(CF_3SO_2)_2N^-$ in terms of providing good resist resolution or good pattern shape, in particular, preferably represents $(CF_3CF_2)_3PF_3^-$, nonafluorobutanesulfonate anion, $(C_6F_5)_4B^-$, $((CF_3)_2C_6H_3)_4B^-$, and $(CF_3SO_2)_3C^-$ in view of good compatibility with resist compositions. Also, in important application of cured product transparency, $X^-$ preferably represents $(C_6F_5)_4Ga^-$ in view of good heat-resistant transparency The sulfonium salt may be produced by Production Process described below.

[Chemical Formula 4]

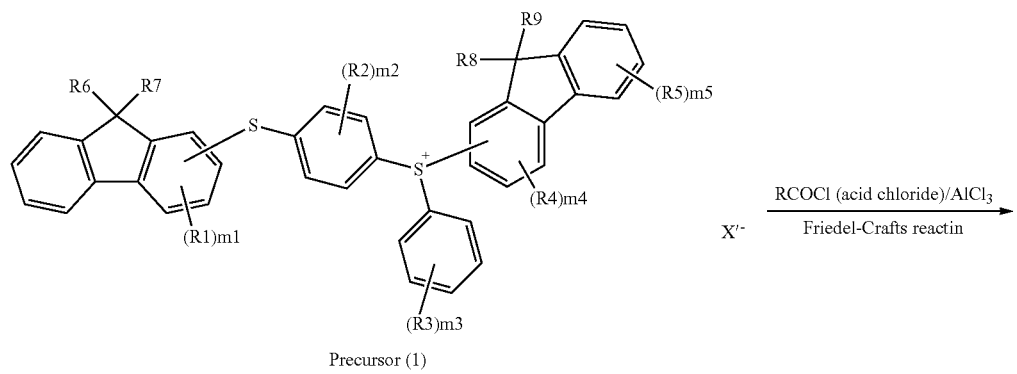

Precursor (1)

-continued

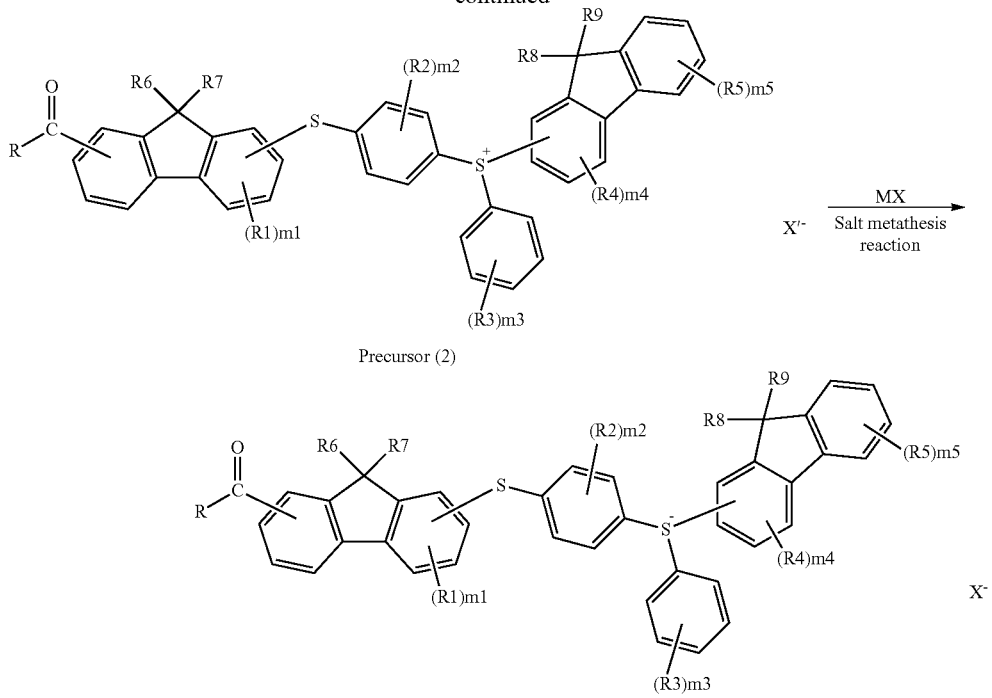

Precursor (2)

In the above reaction formula, R, R1 to R9, X⁻, and m1 to m5 have the same definitions as those in formula (1).

Al represents an aluminum atom, Cl represents a chlorine atom, X' represents a monovalent polyatomic anion. Examples of X' include methanesulfonate anion, perfluoroalkylsulfonate anion, and hydrogen sulfate anion.

The monovalent polyatomic anion (X'⁻) can be replaced with another anion (X⁻) according to the invention, for example, by a metathesis reaction as shown above.

MX represents a salt of an alkali metal (such as lithium, sodium, or potassium) cation with another anion according to the invention (such as an anion represented by $MY_a^-$, $(Rf)_bPF_{6-b}^-$, $R^{10}{}_cBY_{4-c}^-$, $R^{10}{}_cGaY_{4-c}^-$, $R^{11}SO_3^-$, $(R^{11}SO_2)_3C^-$, or $(R^{11}SO_2)_2N^-$).

In the above reaction formula, the first step reaction may be performed in the absence of a solvent, or if necessary, may be performed in an organic solvent (general solvent used for Friedel-Crafts reaction such as acetonitrile, tetrahydrofuran, dioxane, ethanol, or acetone). The reaction temperature may be about −20 to 150° C., depending on the boiling point of used solvent. The reaction time may be about 1 to several tens of hours.

The second step reaction may be performed continuously after the first step or performed after a precursor (2) is isolated (and purified if necessary). The precursor (2) is mixed and stirred with an aqueous solution of the salt (MX) of an alkali metal cation with a monovalent polyatomic anion so that it is subjected to a metathesis reaction, and the precipitated solid is separated by filtration, or the separated oil product is extracted with an organic solvent, and the solvent is removed, so that the sulfonium salt of the invention is obtained in the form of a solid or a viscous liquid. If necessary, the resulting solid or viscous liquid may be purified by washing with an appropriate organic solvent, recrystallization technique, or column chromatography.

The chemical structure of the sulfonium salt of the invention can be identified by a common analysis method or methods (such as $^1$H-, $^{11}$B-, $^{13}$C-, $^{19}$F-, $^{31}$P-nuclear magnetic resonance spectroscopy, infrared absorption spectroscopy, and/or elemental analysis).

The photoacid generator of the present invention comprises the sulfonium salt represented by formula (1), and may be used as it is or in combination with an additional conventionally known photoacid generator.

When an additional photoacid generator is contained, the content (% by mole) of the additional photoacid generator is preferably from 0.1 to 100, more preferably from 0.5 to 50, based on the total molar number of the sulfonium salt represented by formula (1) of the present invention.

Examples of the additional photoacid generator include conventionally known ones such as onium salts (such as sulfonium, iodonium, selenium, ammonium, and phosphonium) and salts of transition metal complex ions with anions.

The sulfonium salt represented by formula (1) may be previously dissolved in a solvent that does not inhibit polymerization, crosslinking reaction and deprotection reaction so that it can be easily dissolved in a cationically polymerizable compound or a chemically amplified photoresist composition.

Examples of the solvent include carbonates such as propylene carbonate, ethylene carbonate, 1,2-butylene carbonate, dimethyl carbonate, and diethyl carbonate; ketones such as acetone, methyl ethyl ketone, cyclohexanone, methyl isoamyl ketone, and 2-heptanone; polyhydric alcohols and derivatives thereof, such as monomethyl ethers, monoethyl ethers, monopropyl ethers, monobutyl ethers, or monophenyl ethers of ethylene glycol, ethylene glycol monoacetate, diethylene glycol, diethylene glycol monoacetate, propylene glycol, propylene glycol monoacetate, dipropylene glycol, and dipropylene glycol monoacetate; cyclic ethers such as dioxane; esters such as ethyl formate, methyl lactate, ethyl lactate, methyl acetate, ethyl acetate, butyl acetate, methyl pyruvate, methyl acetoacetate, ethyl acetoacetate, ethyl pyruvate, ethyl ethoxyacetate, methyl methoxypropionate, ethyl ethoxypropionate, methyl 2-hydroxypropionate, ethyl 2-hydroxypropionate, ethyl 2-hydroxy-2-methylpropionate, methyl 2-hydroxy-3-methylbutanoate, 3-methoxybutyl acetate, and 3-methyl-3-methoxybutyl acetate; and aromatic hydrocarbons such as toluene and xylene.

When a solvent is used, the amount of the solvent used is preferably from 15 to 1,000 parts by weight, more preferably from 30 to 500 parts by weight, based on 100 parts by weight of the sulfonium salt represented by formula (1) of the present invention. These solvents may be used alone or in combination of two or more.

The energy ray-curable composition of the present invention comprises the above photoacid generator and a cationically polymerizable compound.

Examples of the cationically polymerizable compound as a constituent of the energy ray-curable composition include cyclic ethers (such as epoxide and oxetane), ethylenically unsaturated compounds (such as vinyl ether and styrene), bicycloorthoesters, spiroorthocarbonates, and spiroorthoesters (such as those described in JP-A No. 11-060996, JP-A No. 09-302269, JP-A No. 2003-026993).

Known epoxides and the like may be used as epoxides, example of which include aromatic epoxides, alicyclic epoxides, and aliphatic epoxides.

Examples of the aromatic epoxides include glycidyl ethers of monohydric or polyhydric phenols having at least one aromatic ring (such as phenol, bisphenol A, phenol novolac, and alkylene oxide adducts thereof).

Examples of the alicyclic epoxides include compounds obtained by epoxidation of compounds having at least one cyclohexene or cyclopentene ring with an oxidizing agent (such as 3,4-epoxycyclohexylmethyl-3,4-epoxycyclohexanecarboxylate).

Examples of the aliphatic epoxides include polyglycidyl ethers of aliphatic polyhydric alcohols or alkylene oxide adducts thereof (such as 1,4-butanediol diglycidyl ether and 1,6-hexanediol diglycidyl ether), polyglycidyl esters of aliphatic polybasic acids (such as diglycidyl tetrahydrophthalate), and epoxidized long-chain unsaturated compounds (such as epoxidized soybean oil and epoxidized polybutadiene).

Known oxetanes and the like may be used as oxetanes, examples of which include 3-ethyl-3-hydroxymethyloxetane, 2-ethylhexyl(3-ethyl-3-oxetanylmethyl)ether, 2-hydroxyethyl(3-ethyl-3-oxetanylmethyl)ether, 2-hydroxypropyl(3-ethyl-3-oxetanylmethyl)ether, 1,4-bis[(3-ethyl-3-oxetanylmethoxy)methyl]benzene, oxetanylsilsesquioxetane, and phenol novolac oxetane.

Known cationically polymerizable monomers and the like may be used as ethylenically unsaturated compounds, examples of which include aliphatic monovinyl ethers, aromatic monovinyl ethers, polyfunctional vinyl ethers, styrenes, and cationically polymerizable nitrogen-containing monomers.

Examples of the aliphatic monovinyl ethers include methyl vinyl ether, ethyl vinyl ether, butyl vinyl ether, and cyclohexyl vinyl ether.

Examples of the aromatic monovinyl ethers include 2-phenoxyethyl vinyl ether, phenyl vinyl ether, and p-methoxyphenyl vinyl ether.

Examples of the polyfunctional vinyl ethers include butanediol-1,4-divinyl ether and triethylene glycol divinyl ether.

Examples of the styrenes include styrene, α-methylstyrene, p-methoxystyrene, and p-tert-butoxystyrene.

Examples of the cationically polymerizable nitrogen-containing monomers include N-vinylcarbazole and N-vinylpyrrolidone.

Examples of the bicycloorthoesters include 1-phenyl-4-ethyl-2,6,7-trioxabicyclo[2.2.2]octane and 1-ethyl-4-hydroxymethyl-2,6,7-trioxabicyclo[2.2.2]octane.

Examples of the spiroorthocarbonates include 1,5,7,11-tetraoxaspiro[5.5]undecane and 3,9-dibenzyl-1,5,7,11-tetraoxaspiro[5.5]undecane.

Examples of the spiroorthoesters include 1,4,6-trioxaspiro[4.4]nonane, 2-methyl-1,4,6-trioxaspiro[4.4]nonane, and 1,4,6-trioxaspiro[4.5]decane.

Additional example of the cationically polymerizable compound includes polyorganosiloxanes having at least one cationically polymerizable group in a molecule (such as those described in JP-A 2001-348482, Journal of Polym. Sci., Part A, Polym. Chem., Vol. 28,497 (1990)). These polyorganosiloxanes may be straight chain, branched chain, cyclic, or the mixture of these.

Among these cationically polymerizable compounds, epoxides, oxetanes, and vinyl ethers are preferred, epoxides and oxetane are more preferred, and alicyclic epoxides and oxetanes are particularly preferred. These cationically polymerizable compounds may be used alone or in combination of two or more.

The content of the sulfonium salt represented by formula (1) of the invention in an energy ray-curable composition is preferably from 0.05 to 20 parts by weight, more preferably from 0.1 to 10 parts by weight, based on 100 parts by weight of the cationically polymerizable compound. Within the range, the cationically polymerizable compound can be more sufficiently polymerized, so that the physical properties of the cured product can be further improved. It will be understood that the content may be determined taking into account various factors such as the properties of the cationically polymerizable compound, the type and irradiation dose of the energy ray, the temperature, the curing time, the humidity, and the thickness of the coating film, and is not limited to the above range.

If necessary, the energy ray-curable composition of the invention may contain known additives (such as a sensitizer, a pigment, a filler, an antistatic agent, a flame retardant, an anti-foaming agent, a fluidity controlling agent, a light stabilizer, an antioxidant, a tackifier, an ion scavenger, an anti-coloring agent, a solvent, a nonreactive resin, and a radically-polymerizable compound).

Known sensitizers (such as those described in JP-A No. 11-279212 and JP-A No. 09-183960) and the like may be used as such a sensitizer, examples of which include anthracenes {such as anthracene, 9,10-dibutoxyanthracene, 9,10-dimethoxyanthracene, 9,10-diethoxyanthracene, 2-ethyl-9,10-dimethoxyanthracene, and 9,10-dipropoxyanthracene}; pyrene; 1,2-benzanthracene; perylene; tetracene; coronene; thioxanthones {such as thioxanthone, 2-methylthioxanthone, 2-ethylthioxanthone, 2-chlorothioxanthone, 2-isopropylthioxanthone, and 2,4-diethylthioxanthone}; phenothiazine {such as phenothiazine, N-methylphenothiazine, N-ethylphenothiazine, and N-phenylphenothiazine}; xanthone; naphthalenes {such as 1-naphthol, 2-naphthol, 1-methoxynaphthalene, 2-methoxynaphthalene, 1,4-dihydroxynaphthalene, and 4-methoxy-1-naphthol}; ketones {such as dimethoxyacetophenone, diethoxyacetophenone, 2-hydroxy-2-methyl-1-phenylpropan-1-one, 4'-isopropyl-2-hydroxy-2-methylpropiophenone, and 4-benzoyl-4'-methyl-diphenylsulfide}; carbazoles {such as N-phenylcarbazole, N-ethylcarbazole, poly-N-vinylcarbazole, and N-glycidylcarbazole}; chrysenes {such as 1,4-dimethoxychrysene and 1,4-di-α-methylbenzyloxychrysene}; and phenanthrenes {such as 9-hydroxyphenanthrene, 9-methoxyphenanthrene, 9-hydroxy-10-methoxyphenanthrene, and 9-hydroxy-10-ethoxyphenanthrene}.

When a sensitizer is contained, the content of the sensitizer is preferably from 1 to 300 parts by weight, more preferably from 5 to 200 parts by weight, based on 100 parts of the photoacid generator of the invention.

Known pigments and the like may be used as pigments, examples of which include inorganic pigments (such as titanium oxide, iron oxide, and carbon black) and organic pigments (such as azo pigments, cyanine pigments, phthalocyanine pigments, and quinacridone pigments).

When a pigment is contained, the content of the pigment is preferably from 0.5 to 400,000 parts by weight, more preferably from 10 to 150,000 parts by weight, based on 100 parts of the photoacid generator of the invention.

Known fillers and the like may be used as fillers, examples of which include fused silica, crystalline silica, calcium carbonate, aluminum oxide, aluminum hydroxide, zirconium oxide, magnesium carbonate, mica, talc, calcium silicate, and lithium aluminum silicate.

When a filler is contained, the content of the filler is preferably from 50 to 600,000 parts by weight, more preferably 300 to 200,000 parts by weight, based on 100 parts of the photoacid generator of the invention.

Known antistatic agents and the like may be used as antistatic agents, examples of which include nonionic antistatic agents, anionic antistatic agents, cationic antistatic agents, ampholytic antistatic agents, and high molecular weight antistatic agents.

When an antistatic agent is contained, the content of the antistatic agent is preferably from 0.1 to 20,000 parts by weight, more preferably from 0.6 to 5,000 parts by weight, based on 100 parts of the photoacid generator of the invention.

Known flame retardants and the like may be used as flame retardants, examples of which include inorganic flame retardants {such as antimony trioxide, antimony pentoxide, tin oxide, tin hydroxide, molybdenum oxide, zinc borate, barium metaborate, red phosphorus, aluminum hydroxide, magnesium hydroxide, and calcium aluminate}; bromine flame retardants {such as tetrabromophthalic anhydride, hexabromobenzene, and decabromobiphenyl ether}; and phosphate flame retardants {such as tris(tribromophenyl) phosphate}.

When a flame retardant is contained, the content of the flame retardant is preferably from 0.5 to 40,000 parts by weight, more preferably from 5 to 10,000 parts by weight, based on 100 parts of the photoacid generator of the invention.

Known anti-foaming agents and the like may be used as anti-foaming agents, examples of which include alcoholic anti-foaming agents, metallic soap anti-foaming agents, phosphate anti-foaming agents, fatty acid ester anti-foaming agents, polyether anti-foaming agents, silicone anti-foaming agents, and mineral oil anti-foaming agents.

Known fluidity controlling agents and the like may be used as fluidity controlling agents, examples of which include hydrogenated castor oil, oxidized polyethylene, organic bentonite, colloidal silica, amide wax, metallic soap, and acrylic ester polymers.

Known light stabilizers and the like may be used as light stabilizers, examples of which include ultraviolet absorbing stabilizers {such as benzotriazole, benzophenone, salicylates, cyanoacrylates, and derivatives thereof}; radical scavenging stabilizers {such as hindered amines}; and quenching stabilizers {such as nickel complexes}.

Known antioxidants and the like may be used as antioxidants, examples of which include phenolic antioxidants (such as monophenolic, bisphenolic, and macromolecular phenolic antioxidants), sulfur-based antioxidants, and phosphorus-based antioxidants.

Known tackifiers and the like may be used as tackifiers, example of which include coupling agents, silane coupling agents, and titanium coupling agents.

Known ion scavenger and the like may be used as ion scavenger, examples of which include organoaluminum (such as alkoxyaluminum and phenoxyaluminum).

Known anti-coloring agents and the like may be used as anti-coloring agents, and antioxidants are generally effective, examples of which include phenolic antioxidants (such as monophenolic, bisphenolic, and macromolecular phenolic antioxidants), sulfur-based antioxidants, and phosphorus-based antioxidants. However, these anti-coloring agents do not have coloring prevention effect on heat resistance test at high temperature.

When an anti-foaming agent, a fluidity controlling agent, a light stabilizer, an antioxidant, a tackifier, an ion scavenger, or an anti-coloring agent is contained, the content of each material is preferably from 0.1 to 20,000 parts by weight, more preferably from 0.5 to 5,000 parts by weight, based on 100 parts of the photoacid generator of the invention.

Any solvent that can be used to dissolve the cationically polymerizable compound or to control the viscosity of the energy ray-curable composition may be used as solvents, examples of which include those listed for the above photoacid generator.

When a solvent is contained, the content of the solvent is preferably from 50 to 2,000,000 parts by weight, more preferably from 200 to 500,000 parts by weight, based on 100 parts of the photoacid generator of the invention.

Examples of the nonreactive resin include polyester, polyvinyl acetate, polyvinyl chloride, polybutadiene, polycarbonate, polystyrene, polyvinyl ether, polyvinyl butyral, polybutene, hydrogenated styrene-butadiene block copolymers, copolymers of (meth)acrylic acid esters, and polyurethane. The number average molecular weight of these resins is preferably from 1,000 to 500,000, more preferably from 5,000 to 100,000 (the number average molecular weight is a value measured by a general method such as GPC).

When a nonreactive resin is contained, the content of the nonreactive resin is preferably from 5 to 400,000 parts by weight, more preferably from 50 to 150,000 parts by weight, based on 100 parts of the photoacid generator of the invention.

When a nonreactive resin is contained, it is preferably dissolved in advance in a solvent so that it can be easily dissolved in the cationically polymerizable compound or the like.

Known radically polymerizable compounds and the like may be used as radically polymerizable compounds {such as those described in "Photopolymer Handbook" edited by The Technical Association of Photopolymers, Japan (1989, Kogyo Chosakai Publishing, Co., Ltd.), "UV/EB Koka Gijutsu" (Technology of UV/EB Curing), edited by Sogo Gijutsu Center (1982, SogoGijutsu Center), "UV/EB Koka Zairyo" (UV/EB Curable Materials), edited by RadTech Japan (1992, CMC), and "UV-Koka niokeru Koka-Furyo/Sogai-Genin to Sonotaisaku" (Causes of UV Curing Defects/Inhibition and Remedies Therefor), edited by TECHNICAL INFORMATION INSTITUTE (2003, TECHNICAL INFORMATION INSTITUTE CO., LTD.)}, examples of which include monofunctional monomers, bifunctional monomers, polyfunctional monomers, epoxy (meth)acrylate, polyester (meth)acrylate, and urethane (meth)acrylate.

When a radically polymerizable compound is contained, the content of the radically polymerizable compound is preferably from 5 to 400,000 parts by weight, more preferably from 50 to 150,000 parts by weight, based on 100 parts of the photoacid generator of the invention.

When a radically polymerizable compound is contained, a radical polymerization initiator initiating polymerization with heat or light is preferably used so that the compound can be polymerized by radical polymerization.

Known radical polymerization initiators and the like may be used as radical polymerization initiators, examples of which include thermal radical polymerization initiators (such as organic peroxides and azo compounds) and photo-radical polymerization initiators (such as acetophenone-based initiators, benzophenone-based initiators, Michler's ketone-based initiators, benzoin-based initiators, thioxanthone-based initiators, and acylphosphine-based initiators.

When a radical polymerization initiator is contained, the content of the radical polymerization initiator is preferably from 0.01 to 20 parts by weight, more preferably from 0.1 to 10 parts by weight, based on 100 parts of the radically polymerizable compound.

The energy ray-curable composition of the invention may be prepared by uniformly mixing and dissolving the cationically polymerizable compound, the photoacid generator, and if necessary an optional additive(s) at room temperature (about 20 to 30° C.) or if necessary, under heating (about 40 to 90° C.), or by further kneading them with a triple-roll mill or the like.

The energy ray-curable composition of the present invention may be cured by irradiation with energy rays so that a cured product can be obtained.

The energy ray may be of any energy ray as long as it has an energy to induce the decomposition of the photoacid generator of the present invention, preferred examples of which include energy rays in the ultraviolet to visible light region (wavelength: from about 100 to about 800 nm) obtained from a low pressure-, medium pressure-, high pressure-, or ultra high pressure-mercury lamp, a metal halide lamp, an LED lamp, a xenon lamp, a carbon arc lamp, a fluorescent lamp, a semiconductor solid-state laser, an argon laser, a He—Cd laser, a KrF excimer laser, an ArF excimer laser, or an $F_2$ laser. Radiations with a high energy, such as electron beams or X-rays may also be used as the energy rays.

While the energy ray irradiation time is influenced by the intensity of the energy rays or the permeability of the energy rays to the energy ray-curable composition, an energy ray exposure time of about 0.1 to 10 seconds is enough at room temperature (about 20 to 30° C.). However, if the permeability of the energy rays is low or if the thickness of the energy ray-curable composition is large, for example, it is sometimes preferred to spend more time. Most energy ray-curable compositions are cured by cationic polymerization in 0.1 seconds to several minutes after the irradiation with energy rays. If necessary, however, post-curing may be performed by heating at a temperature of room temperature (about 20 to 30° C.) to 200° C. for several seconds to several hours after the irradiation with energy rays.

Specific applications of the energy ray-curable composition of the invention include paints, coating agents, various coating materials (hard coats, anti-fouling coating materials, anti-fogging coating materials, anti-corrosion coating materials, optical fibers and the like), back surface treatment agents for adhesive tapes, release coating materials of release sheets for adhesive labels (release papers, release plastic films, release metal foils and the like), printing plates, ink compositions for dental materials (dental formulations and dental composites), ink compositions, inkjet ink compositions, positive resists (for formation of connection terminals and wiring patterns in production of electronic components such as circuit boards, CSP and MEMS elements), resist films, liquid resists and negative resists (permanent film materials of surface protecting films, interlayer dielectric films, planarizing films for semiconductor elements, and transparent electrode for FPD (ITO, IZO, GZO) etc.), resists for MEMS, positive photosensitive materials, negative photosensitive materials, various adhesives (various temporary fixing agents for electronic components, adhesives for HDD, adhesives for pick-up lenses, adhesives for functional films for FPD (polarizing plates, antireflection films), holographic resins, FPD materials (color filters, black matrices, partition wall materials, photospacers, ribs, orientation films for liquid crystals, sealing agents for FPD and the like), optical members, molding materials (for building materials, optical components and lenses), casting materials, putty materials, glass fiber impregnating agents, fillers, sealing materials, sealants, photosemiconductor (LED) sealing materials, optical waveguide materials, nano-imprint materials, stereolithography materials, and micro-stereolithography materials.

The photoacid generator of the invention, which can generate a strong acid upon irradiation with light, may also be used as a photoacid generator for known chemically amplified resist materials (such as those described in JP-A No. 2003-267968, JP-A No. 2003-261529, and JP-A No. 2002-193925).

Examples of the chemically amplified resist materials include (1) a two-component chemically amplified positive resist comprising, as essential ingredients, a photo-acid generator and a resin that can be made soluble in an alkali developing solution by the action of an acid; (2) a three-component chemically amplified positive resist comprising, as essential ingredients, a resin soluble in an alkali developing solution, a dissolution inhibitor that can be made soluble in an alkali developing solution by the action of an acid, and a photoacid generator; and (3) a chemically amplified negative resist comprising, as essential ingredients, a resin soluble in an alkali developing solution, a crosslinking agent that can crosslink the resin to make the resin insoluble in an alkali developing solution when heated in the presence of an acid, and a photoacid generator.

The chemically amplified positive photoresist composition of the invention contains an ingredient (A) comprising the photoacid generator of the invention, which is a compound generating an acid when the compound is irradiated with light or a radiation; and a resin ingredient (B) increasing its solubility in an alkali under the action of an acid.

In the chemically amplified positive photoresist composition of the invention, the ingredient (A) may be used in combination with an additional known conventional photoacid generator. Examples of the additional photoacid generator include onium salt compounds, sulfone compounds, sulfonate compounds, sulfonimide compounds, disulfonyl diazomethane compounds, disulfonylmethane compounds, oxime sulfonate compounds, hydrazine sulfonate compounds, triazine compounds, and nitrobenzyl compounds, as well as organohalogen compounds and disulfone.

The additional known conventional photoacid generator is preferably at least one from the group of an onium compound, a sulfonimide compound, a diazomethane compound, and an oxime sulfonate compound.

When such an additional known conventional photoacid generator is used in combination, the amount of the additional photoacid generator used is generally from 10 to 900 parts by weight, preferably from 25 to 400 parts by weight, based on 100 parts by weight of the total amount of the sulfonium salts represented by formula (1) described above, although the amount thereof may be arbitrary.

The content of the above ingredient (A) is preferably from 0.05 to 5% by weight, in the solids of the chemically amplified positive photoresist composition.

<Resin Ingredient (B) Increasing its Solubility in an Alkali Under the Action of an Acid>

The aforesaid "resin (B) increasing its solubility in an alkali under the action of an acid" (hereinafter referred to as "ingredient (B)" in the description), which is used in the chemically amplified positive photoresist composition of the invention for thick films, is at least one resin selected from the group consisting of a novolac resin (B1), a polyhydroxystyrene resin (B2), and an acrylic resin (B3), or a mixture thereof, or a copolymer thereof.

[Novolac Resin (B1)]

The novolac resin (B1) to be used may be a resin represented by general formula (b1) described below.

[Chemical Formula 5]

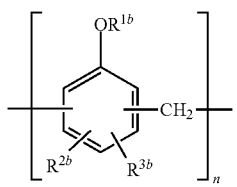

(b1)

In general formula (b1) described above, $R^{1b}$ represents an acid-dissociating solubility-inhibiting group, $R^{2b}$ and $R^{3b}$ each independently represent a hydrogen atom or an alkyl group having 1 to 6 carbon atoms, and n represents the number of repeating units of the structure in the parentheses.

The above acid-dissociating solubility-inhibiting group represented by $R^{1b}$ is preferably a straight chain alkyl group having 1 to 6 carbon atoms, a branched chain alkyl group having 3 to 6 carbon atoms, a cyclic alkyl group having 3 to 6 carbon atoms, a tetrahydropyranyl group, a tetrahydrofuranyl group, or a trialkylsilyl group.

Specific examples of the above acid-dissociating solubility-inhibiting group represented by $R^{1b}$ include a methoxyethyl group, an ethoxyethyl group, a n-propoxyethyl group, an isopropoxyethyl group, a n-butoxyethyl group, an isobutoxyethyl group, a tert-butoxyethyl group, a cyclohexyloxyethyl group, a methoxypropyl group, an ethoxypropyl group, a 1-methoxy-1-methyl-ethyl group, a 1-ethoxy-1-methyl-ethyl group, a tert-butoxycarbonyl group, a tert-butoxycarbonylmethyl group, a trimethylsilyl group, and a tri-tert-butyldimethylsilyl group.

[Polyhydroxystyrene Resin (B2)]

The polyhydroxystyrene resin (B2) to be used may be a resin represented by general formula (b4) described below.

[Chemical Formula 6]

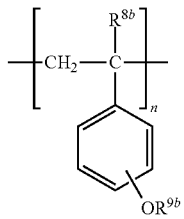

(b4)

In general formula (b4) described above, $R^{8b}$ represents a hydrogen atom or an alkyl group having 1 to 6 carbon atoms, $R^{9b}$ represents an acid-dissociating solubility-inhibiting group, and n represents the number of repeating units of the structure in the parentheses.

The above alkyl group having 1 to 6 carbon atoms may be a straight chain alkyl group having 1 to 6 carbon atoms, a branched chain alkyl group having 3 to 6 carbon atoms, or a cyclic alkyl group having 3 to 6 carbon atoms. Specifically, it may be a methyl group, an ethyl group, a propyl group, an isopropyl group, a n-butyl group, an isobutyl group, a tert-butyl group, a pentyl group, an isopentyl group, or a neopentyl group, and the cyclic alkyl group may be a cyclopentyl group or a cyclohexyl group.

Examples of the above acid-dissociating solubility-inhibiting group represented by $R^{9b}$ which may be used include those listed for $R^{1b}$ described above.

The polyhydroxystyrene resin (B2) may further comprise, as a structural unit, an additional polymerizable compound for properly controlling the physical and chemical properties. Such a polymerizable compound may be a known radically polymerizable or anionically polymerizable compound. Examples thereof include monocarboxylic acids such as acrylic acid; dicarboxylic acids such as maleic acid, fumaric acid, and itaconic acid; methacrylic acid derivatives having a carboxyl group and an ester bond, such as 2-methacryloyloxyethylsuccinic acid; alkyl (meth)acrylates such as methyl (meth)acrylate; hydroxyalkyl (meth)acrylates such as 2-hydroxyethyl (meth)acrylate; dicarboxylic acid diesters such as diethyl maleate; vinyl group-containing aromatic compounds such as styrene and vinyl toluene; vinyl group-containing aliphatic compounds such as vinyl acetate; conjugated diolefins such as butadiene and isoprene; nitrile group-containing polymerizable compounds such as acrylonitrile; chlorine-containing polymerizable compounds such as vinyl chloride; and amide bond-containing polymerizable compounds such as acrylamide.

[Acrylic Resin (B3)]

The acrylic resin (B3) to be used may be any of resins represented by general formulae (b5) to (b10) described below.

[Chemical Formula 7]

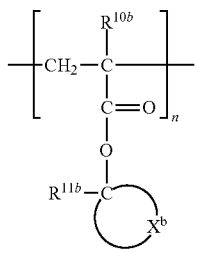

(b5)

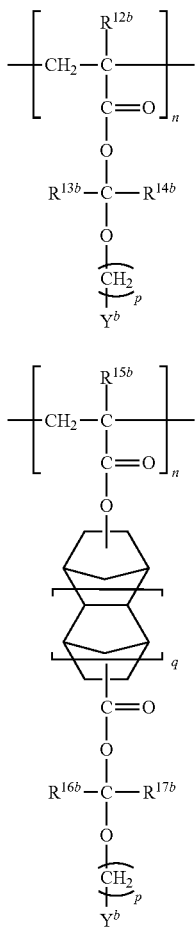

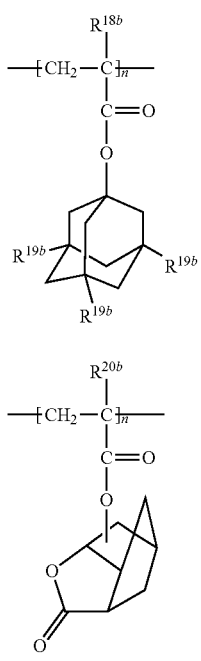

[Chemical Formula 8]

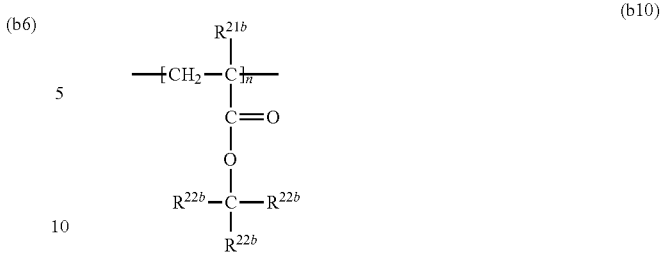

In general formulae (b5) to (b7) described above, $R^{10b}$ to $R^{17b}$ each independently represent a hydrogen atom, a straight chain alkyl group having 1 to 6 carbon atoms, a branched chain alkyl group having 3 to 6 carbon atoms, a fluorine atom, a straight chain fluorinated alkyl group having 1 to 6 carbon atoms, or a branched chain fluorinated alkyl group having 3 to 6 carbon atoms, $X^b$ represents a moiety that forms a hydrocarbon ring of 5 to 20 carbon atoms with the carbon atom bonded to the moiety, $Y^b$ represents an optionally substituted aliphatic cyclic group or an optionally substituted alkyl group, n represents the number of repeating units of the structure in the parentheses, p represents an integer of 0 to 4, and q represents 0 or 1.

In general formulae (b8), (b9), and (b10), $R^{18b}$, $R^{20b}$, and $R^{21b}$ each independently represent a hydrogen atom or a methyl group. In general formula (b8), each occurrence of $R^{19b}$ independently represents a hydrogen atom, a hydroxyl group, a cyano group, or a $COOR^{23b}$ group (wherein $R^{23b}$ represents a hydrogen atom, a straight chain alkyl group having 1 to 4 carbon atoms, a branched chain alkyl group having 3 to 4 carbon atoms, or a cycloalkyl group having 3 to 20 carbon atoms). In general formula (b10), each occurrence of $R^{22b}$ independently represents a monovalent alicyclic hydrocarbon group having 4 to 20 carbon atoms or a derivative thereof, a straight chain alkyl group having 1 to 4 carbon atoms, or a branched chain alkyl group having 3 to 4 carbon atoms, wherein at least one of $R^{22b}$ is the alicyclic hydrocarbon group or a derivative thereof, or any two of $R^{22b}$, together with the common carbon atom to which they are each bonded, join to form a bivalent alicyclic hydrocarbon group having 4 to 20 carbon atoms or a derivative thereof, and the remaining $R^{22b}$ moieties are a straight chain alkyl group having 1 to 4 carbon atoms, a branched chain alkyl group having 3 to 4 carbon atoms, or a monovalent alicyclic hydrocarbon group having 4 to 20 carbon atoms or a derivative thereof.

Among the above ingredients (B), the acrylic resin (B3) is preferably used.

The polystyrene-equivalent weight average molecular weight of the ingredient (B) is preferably from 10,000 to 600,000, more preferably from 50,000 to 600,000, even more preferably from 230,000 to 550,000. When it has such a weight average molecular weight, the resist resin can have excellent physical properties.

The ingredient (B) is also preferably a resin with a dispersity of 1.05 or more. As used herein, the term "dispersity" refers to a value obtained by dividing the weight average molecular weight by the number average molecular weight. When the dispersity is such a value, the resist can have high plating resistance and the resist resin can have excellent physical properties.

The content of the above ingredient (B) is preferably from 5 to 60% by weight, in the solids of the chemically amplified positive photoresist composition.

<Alkali-Soluble Resin (C)>

The chemically amplified positive photoresist composition of the invention preferably further contains an alkali-soluble resin (referred to as "ingredient (C)" in the description) for improving the physical properties of the resist resin. The ingredient (C) is preferably at least one selected from the group consisting of a novolac resin, a polyhydroxystyrene resin, an acrylic resin, and a polyvinyl resin.

The content of the above ingredient (C) is preferably from 5 to 95 parts by weight, more preferably from 10 to 90 parts by weight, based on 100 parts by weight of the above ingredient (B). When it is 5 parts by weight or more, the physical properties of the resist resin can be improved, and if it is 95 parts by weight or less, film loss during development will tend to be prevented.

<Acid Diffusion Controlling Agent (D)>

The chemically amplified positive photoresist composition of the invention for thick films preferably further contains an acid diffusion controlling agent (D) (referred to as "ingredient (D)" in the description) for improving the shape of the resist pattern and post exposure delay time stability. The ingredient (D) is preferably a nitrogen-containing compound, and if necessary, may contain an organic carboxylic acid, or a phosphorous oxo acid or a derivative thereof.

The chemically amplified positive photoresist composition of the invention may further contain an adhesion auxiliary agent for improving adhesion to the substrate. A functional silane coupling agent is preferable as the adhesion auxiliary agent to be used.

The chemically amplified positive photoresist composition of the invention may further contain a surfactant for improving coating properties, anti-foaming properties, leveling properties, or the like.

The chemically amplified positive photoresist composition of the invention may further contain an acid, an acid anhydride, or a high-boiling-point solvent for fine adjustment of its solubility in an alkali developing solution.

The chemically amplified positive photoresist composition of the invention, which does not basically need a sensitizer, may also contain a sensitizer for complementing the sensitivity, if necessary. A known conventional sensitizer may be used as such a sensitizer, specific examples of which include aforesaid sensitizers.

The amount of the sensitizer used may be from 5 to 500 parts by weight, preferably from 10 to 300 parts by weight, based on 100 parts by weight of the total amount of the sulfonium salts represented by formula (1) described above.

Also, the chemically amplified positive photoresist composition of the invention may appropriately contain an organic solvent for adjusting viscosity. Specific examples of the organic solvent include aforesaid solvents.

The amount of the organic solvent used is preferably in such a range that the solids content of the chemically amplified positive photoresist composition of the invention is 30% by weight or more so that a photoresist layer with a thickness of 5 μm or more is obtained using the composition (for example, by spin coating).

For example, the chemically amplified positive photoresist composition of the invention for thick films can be prepared only by mixing or stirring the above ingredients using a conventional method, and if necessary, the ingredients may be dispersed or mixed using a disperser such as a dissolver, a homogenizer, or a three-roll mill. After the mixing, the product may be further filtered using a mesh, a membrane filter, or the like.

The chemically amplified positive photoresist composition of the invention is suitable for forming a photoresist layer with a thickness of generally 5 to 150 μm, more preferably 10 to 120 μm, even more preferably 10 to 100 μm, on a support. The resulting photoresist laminate comprises the support and a photoresist layer that is placed on the support and comprises the chemically amplified positive photoresist composition of the invention.

The support is not particularly limited, and any known conventional support may be used, examples of which include a substrate for electronic parts and a product produced by forming a given wiring pattern on the substrate. Examples of such a substrate include a substrate made of silicon, silicon nitride, or metal such as titanium, tantalum, palladium, titanium-tungsten, copper, chromium, iron, or aluminum, and a glass substrate. In particular, the use of the chemically amplified positive photoresist composition of the invention makes it possible to successfully form a resist pattern even on a copper substrate. Examples of materials that may be used for wiring pattern include copper, solder, chromium, aluminum, nickel, and gold.

For example, the above photoresist laminate may be produced as described below. Specifically, a solution of the chemically amplified positive photoresist composition prepared as described above is applied to the support, and the solvent is removed by heating, so that a desired coating film is formed. The application to the support may be performed by spin coating, slit coating, roll coating, screen printing, applicator method, or any other application method. The coating film of the composition of the invention may be prebaked under the conditions of generally 70 to 150° C., preferably 80 to 140° C., and about 2 to 60 minutes, which depend on the type or formulation rate of each ingredient in the composition, the thickness of the coating, or the like.

The thickness of the photoresist layer may be generally in the range of 5 to 150 μm, preferably 10 to 120 μm, more preferably 10 to 100 μm.

In order to form a resist pattern using the photoresist laminate obtained as described above, the resulting photoresist layer may be site-selectively irradiated with (or exposed to) light or a radiation, such as an ultraviolet ray or visible light with a wavelength of 300 to 500 nm.

As used herein, "light" may be of any type activating the acid generator to generate an acid and are intended to include ultraviolet rays, visible light, or far ultraviolet rays, and "radiations" means X-rays, electron beams, ion beams, or the like. Examples of sources for light or radiations that may be used include low-pressure mercury lamps, high-pressure mercury lamps, ultra high-pressure mercury lamps, metal halide lamps, argon gas lasers, and LED lamps. The irradiation dose may be from 50 to 10,000 mJ/cm$^2$, for example, when an ultra high-pressure mercury lamp is used, although the irradiation dose depends on the type or formulation amount of each ingredient in the composition, the thickness of the coating film, or the like.

After the exposure, heating is performed using a known method to enhance the diffusion of the acid, so that the alkali solubility of the exposed part of the photoresist layer is changed. Subsequently, the unnecessary part is dissolved or removed, for example, using a given alkaline aqueous solution as a developer, so that a desired resist pattern is obtained.

While the development time depends on the type or formulation rate of each ingredient in the composition, or the dry coating thickness of the composition, it is generally from 1 to 30 minutes. The development method may be any of a puddle development method, a dipping method, a puddle method, and a spray development method. After the development, washing with flowing water is performed for 30 to 90 seconds, and drying is performed using an air gun, an oven, or the like.

A conductor such as a metal is embedded, for example, by plating or the like, in the non-resist part (where the resist has been removed using the alkali developing solution) of the resist pattern obtained as described above so that a joining terminal such as a metal post or bump can be formed. The plating method is not particularly restricted, and various known conventional plating methods may be used. The plating solution to be used is preferably a solder, copper, gold, or nickel plating solution. The remaining resist pattern is finally removed by a conventional method using a liquid stripper or the like.

The chemically amplified positive photoresist composition of the invention may also be used to form a dry film. Such a dry film comprises a layer comprising the chemically amplified positive photoresist composition of the invention; and protective films formed on both sides of the layer. The layer comprising the chemically amplified positive photoresist composition may generally have a thickness in the range of 10 to 150 preferably 20 to 120 more preferably 20 to 80 μm. The protective films are not particularly restricted, and resin films that have been used in conventional dry films may be used. In one case, one may be a polyethylene terephthalate film, and the other may be one selected from the group consisting of a polyethylene terephthalate film, a polypropylene film, and a polyethylene film.

For example, the chemically amplified positive dry film as described above may be produced as described below. Specifically, a solution of the chemically amplified positive photoresist composition prepared as described above is applied to one of the protective films, and the solvent is removed by heating, so that a desired coating film is formed. The drying conditions may be generally 60 to 100° C. and about 5 to 20 minutes, although they depend on the type or formulation rate of each ingredient in the composition, the thickness of the coating film, or the like.

A process of forming a resist pattern using the chemically amplified dry film obtained as described above may include stripping off one of the protective films from the chemically amplified positive dry film, laminating the resulting film on a support in such a manner that the exposed surface faces the above support side, so that a photoresist layer is obtained, then performing prebaking to dry the resist, and then stripping off the other protective film.

The resulting photoresist layer provided on the support in such a manner may be subjected to the same process as described above for the photoresist layer formed by direct application to the support so that a resist pattern can be formed.

The chemically amplified negative photoresist composition of the invention contains an ingredient (E) comprising the photoacid generator of the invention, which is a compound generating an acid when irradiated with light or a radiation; an alkali-soluble resin (F) having a phenolic hydroxyl group; and a crosslinking agent (G).

The ingredient (E) comprising the photoacid generator of the invention is the same as the aforesaid ingredient (A).

Alkali-Soluble Resin (F) Having Phenolic Hydroxyl Group

In the invention, examples of the "alkali-soluble resin having a phenolic hydroxyl group" (hereinafter referred to as "phenolic resin (F)"), which may be used, include a novolac resin, polyhydroxystyrene, a polyhydroxystyrene copolymer, a copolymer of hydroxystyrene and styrene, a copolymer of hydroxystyrene, styrene, and a (meth)acrylic acid derivative, a phenol-xylylene glycol condensate resin, a cresol-xylylene glycol condensate resin, and a phenol-dicyclopentadiene condensate resin. Among them, preferred are a novolac resin, polyhydroxystyrene, a polyhydroxystyrene copolymer, a copolymer of hydroxystyrene and styrene, a copolymer of hydroxystyrene, styrene, and a (meth)acrylic acid derivative, and a phenol-xylylene glycol condensate resin. These phenolic resins (F) may be used alone or in a mixture of two or more.

The phenolic resin (F) may also contain a low-molecular-weight phenolic compound as a partial component.

Examples of the above low-molecular-weight phenolic compound include 4,4'-dihydroxydiphenylmethane and 4,4'-dihydroxydiphenyl ether.

Crosslinking Agent (G)

In the invention, the "crosslinking agent" (hereinafter also referred to as "crosslinking agent (G)") is not particularly limited as long as it acts as a crosslinking component (curing component) reactive with the aforesaid phenolic resin (F). Examples of the above crosslinking agent (G) include a compound having at least two alkyl-etherified amino groups in the molecule, a compound having at least two alkyl-etherified benzene skeletons in the molecule, an oxirane ring-containing compound, a thiirane ring-containing compound, an oxetanyl group-containing compound, and an isocyanate group-containing compound (including a blocked derivative).

Among these crosslinking agents (G), preferred are a compound having at least two alkyl-etherified amino groups in the molecule or an oxirane ring-containing compound. More preferably, a compound having at least two alkyl-etherified amino groups in the molecule is used in combination with an oxirane ring-containing compound.

In the invention, the amount of the crosslinking agent (G) formulated is preferably from 1 to 100 parts by weight, more preferably from 5 to 50 parts by weight, based on 100 parts by weight of the aforesaid phenolic resin (F). When the amount of the crosslinking agent (G) formulated is from 1 to 100 parts by weight, the curing reaction can sufficiently proceed, so that the resulting cured product can have a good pattern shape with a high resolution and have excellent heat resistance and electric insulation, which is preferred.

When a compound having alkyl-etherified amino groups is used in combination with an oxirane ring-containing compound, the content rate of the oxirane ring-containing compound is preferably 50% by weight or less, more preferably from 5 to 40% by weight, in particular, preferably from 5 to 30% by weight, based on the total amount of the compound having alkyl-etherified amino groups and the oxirane ring-containing compound, which is normalized as 100% by weight.

In this case, the resulting cured film also has excellent chemical resistance without losing the high resolution, which is preferred.

Cross-Linked Fine Particles (H)

The chemically amplified negative photoresist composition of the invention may further contain crosslinked fine particles (hereinafter also referred to as "crosslinked fine particles (H)") for improving the durability and thermal shock resistance of the resulting cured product.

The average particle size of the crosslinked fine particles (H) is generally from 30 to 500 nm, preferably from 40 to 200 nm, more preferably from 50 to 120 nm.

A method of controlling the particle size of the cross-linked fine particles (H) is not particularly limited. For example, when the crosslinked fine particles are synthesized by emulsion polymerization, the number of micelles during the emulsion polymerization may be controlled by the amount of the emulsifying agent used so that the particle size can be controlled.

The average particle size of the crosslinked fine particles (H) is a value obtained by a process that includes diluting a dispersion of the crosslinked fine particles by a conventional method and measuring the dilution with a light scattering particle size analyzer or the like.

The amount of the crosslinked fine particles (H) formulated is preferably from 0.5 to 50 parts by weight, more preferably from 1 to 30 parts by weight, based on 100 parts by weight of the aforesaid phenolic resin (F). When the amount of the crosslinked fine particles (H) is from 0.5 to 50 parts by weight, they have excellent compatibility with other ingredients or excellent dispersibility, so that the resulting cured film can have improved thermal shock resistance and heat resistance.

Adhesion Auxiliary Agent

The chemically amplified negative photoresist composition of the invention may also contain an adhesion auxiliary agent for improving adhesion to the base material.

Examples of the above adhesion auxiliary agent include functional silane coupling agents having a reactive substituent such as a carboxyl group, a methacryloyl group, an isocyanate group, or an epoxy group.

The amount of the adhesion auxiliary agent formulated is preferably from 0.2 to 10 parts by weight, more preferably from 0.5 to 8 parts by weight, based on 100 parts by weight of the aforesaid phenolic resin (F). When the amount of the adhesion auxiliary agent formulated is from 0.2 to 10 parts by weight, excellent storage stability and good adhesion can be achieved, which is preferred.

Solvent

The chemically amplified negative photoresist composition of the invention may also contain a solvent for improving the handleability of the resin composition or controlling viscosity or storage stability.

Specific examples of the above solvent include, but are not particularly limited to, those listed above.

The chemically amplified negative photoresist composition of the invention, may also contain a sensitizer, if necessary. A known conventional sensitizer may be used as such a sensitizer, specific examples of which include aforesaid sensitizers.

The amount of the sensitizer used may be from 5 to 500 parts by weight, preferably from 10 to 300 parts by weight, based on 100 parts by weight of the total amount of the sulfonium salts represented by formula (1) described above.

Other Additives

If necessary, the chemically amplified negative photoresist composition of the invention may also contain an additional additive in such an extent that the characteristics of the invention are not impaired. Examples of such an additional additive include an inorganic filler, a sensitizer, a quencher, a leveling agent, and a surfactant.

A method for preparing the chemically amplified negative photoresist composition of the invention is not particularly limited, and it may be prepared by any known method. The composition may also be prepared by placing each ingredient in a sample vial, completely sealing the vial with a plug, and stirring the ingredients on a wave rotor.

The cured product of the invention comprises a product obtained by curing the aforesaid chemically amplified negative photoresist composition.

The chemically amplified negative photoresist composition of the invention described above has high remaining thickness ratio and excellent resolution, and the cured product has excellent electric insulation, thermal shock resistance and the like. Therefore, the cured product is suitable for use as a surface protecting film, a planarizing film, an interlayer dielectric film material, or the like in electronic components such as semiconductor devices and semiconductor packages.

To form the cured product of the invention, the chemically amplified negative photoresist composition of the invention as described above is first applied to a support (such as a resin-bearing copper foil, a copper-clad laminate, a silicon wafer having a sputtered metal film, or an alumina substrate), and the solvent and the like are evaporated by drying, so that a coating film is formed. Subsequently, the coating film is exposed to light through a desired mask pattern and heat-treated (hereinafter the heat treatment is referred to as "PEB") so that the reaction between the phenolic resin (F) and the crosslinking agent (G) is accelerated. The unexposed part is then dissolved and removed by development with an alkaline developing solution, so that a desired pattern is obtained. Heat treatment for producing insulating film characteristics is further performed, so that a cured film is obtained.

An application method such as dipping, spraying, bar coating, roller coating, or spin coating may be used to apply the resin composition to the support. The thickness of the coating film can be appropriately controlled by controlling application means or the solids content or viscosity of a solution of the composition.

Examples of radiations for use in the exposure include ultraviolet rays from low-pressure mercury lamps, high-pressure mercury lamps, metal halide lamps, g-line steppers, h-line steppers, i-line steppers, gh-line steppers, or ghi-line steppers, electron beams, and laser beams. The exposure dose is appropriately selected depending on the light source used, the thickness of the resin film, or the like. For example, in the case of ultraviolet irradiation from a high-pressure mercury lamp, the exposure dose may be from about 100 to 50,000 J/m$^2$ for a resin film thickness of 1 to 50 μm.

After the exposure, the above PEB treatment is performed to accelerate the curing reaction between the phenolic resin (F) and the crosslinking agent (G), which is induced by the generated acid. The PEB conditions are generally 70 to 150° C., preferably 80 to 120° C., and about 1 to 60 minutes, although they depend on the amount of the resin composition formulated, the thickness of the film used, or the like. Subsequently, the unexposed part is dissolved and removed by development with an alkaline developing solution, so that a desired pattern is formed. In this case, the development method may be a shower development method, a spray development method, an immersion development method, a puddle development method, or the like. The development conditions are generally 20 to 40° C. and about 1 to 10 minutes.

After the development, the film may be sufficiently cured by heat treatment so that insulting film characteristics can be sufficiently exerted. The curing conditions are not restricted. Depending on the intended use of the cured product, the composition may be cured by heating at a temperature of 50 to 250° C. for about 30 minutes to 10 hours. Two-stage heating may also be performed so that the curing can sufficiently proceed or deformation of the resulting pattern shape can be prevented. For example, the curing at the first stage may be performed by heating at a temperature of 50 to 120° C. for about 5 minutes to 2 hours, and the curing at the second state may be performed at a temperature of 80 to 250° C. for about 10 minutes to 10 hours. Under such curing conditions, a general oven, an infrared furnace, or the like can be used as the heating equipment.

EXAMPLES

Hereinafter, the invention is more specifically described with reference to Examples, which however are not intended to limit the invention. Hereinafter, "parts" means parts by weight.

[Example 1] Synthesis of {4-[2-(7-acetyl-9,9-dimethylfluorenyl)thio]phenyl}[2-(9,9-dimethylfluorenyl)]phenylsulfonium methanesulfonate (P1-MS)

[Chemical Formula 9]

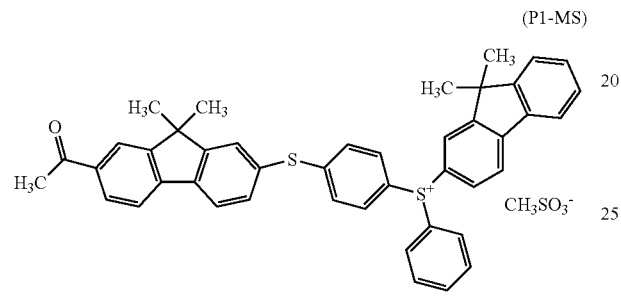

(P1-MS)

Mixed were 7.6 parts of acethyl cloride, 15.5 parts of aluminum cloride and 27.3 parts of dichloromethane, and cooled to 5° C. under stirring. Into the solution, a mixture solution of 15.0 parts of {4-[2-(9,9-dimethylfluorenyl)thio]phenyl}[2-(9,9-dimethylfluorenyl)]phenylsulfonium methanesulfonate and 27.3 parts of dichloromethane were added dropwise slowly. After allowing to react for one hour, the reaction solution was added dropwise into 100 parts of water. Then, the solution was stirred for 30 minutes, and operated to stand for 30 minutes. The water layer was removed, then, 100 parts of water were added into the organic layer, and the solution was stirred and washed. Then, the water layer was removed. After washing five times in total, the organic layer was transferred to a rotary evaporator, and the solvent was removed by distillation, so that P1-MS was obtained as a yellow powder in a yield of 80%. The product was identified by $^1$H-NMR.

[Example 2] Synthesis of {4-[2-(7-acetyl-9,9-dimethylfluorenyl)thio]phenyl}[2-(9,9-dimethylfluorenyl)]phenylsulfonium tris(pentafluoroethyl)trifluorophosphate (P1-FP)

[Chemical Formula 10]

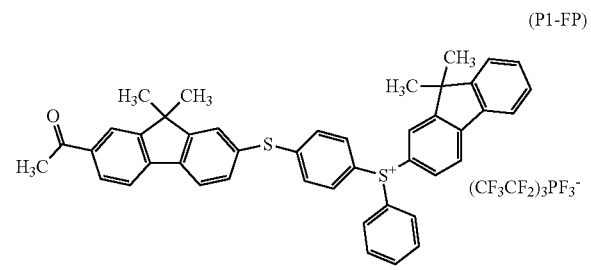

(P1-FP)

Dissolved were 5.0 parts of {4-[2-(7-acetyl-9,9-dimethylfluorenyl)thio]phenyl}[2-(9,9-dimethylfluorenyl)]phenylsulfonium methanesulfonate (P1-MS) synthesized in Example 1 in 34.4 parts of dichloromethane. Into the solution, 3.8 parts of potassium tris(pentafluoroethyl) trifluorophosphate and 30 parts of deionized water were added, and stirred for one hour at room temperature. The organic layer was washed with 30 parts of deionized water five times. The organic layer was transferred to a rotary evaporator, and the solvent was removed by distillation, so that 6.6 parts of P1-FP were obtained as a pale yellow solid in a yield of 90%. The product was identified by $^1$H-NMR and $^{19}$F-NMR.

[Example 3] Synthesis of {4-[2-(7-acetyl-9,9-dimethylfluorenyl)thio]phenyl}[2-(9,9-dimethylfluorenyl)]phenylsulfonium tetrakis(pentafluorophenyl)borate (P1-B)

[Chemical Formula 11]

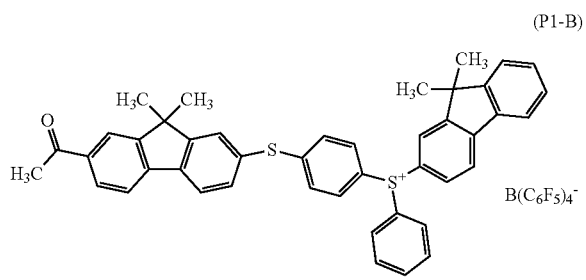

(P1-B)

As in Example 2, 8.0 parts of P1-B were obtained, except that 3.8 parts of potassium tris(pentafluoroethyl) trifluorophosphate in Example 2 were replaced with 5.0 parts of sodium tetrakis(pentafluorophenyl)borate. The product was identified by $^1$H-NMR and $^{19}$F-NMR.

[Example 4] Synthesis of {4-[2-(7-acetyl-9,9-dimethylfluorenyl)thio]phenyl}[2-(9,9-dimethylfluorenyl)]phenylsulfonium hexafluoroantimonate (P1-SB)

[Chemical Formula 12]

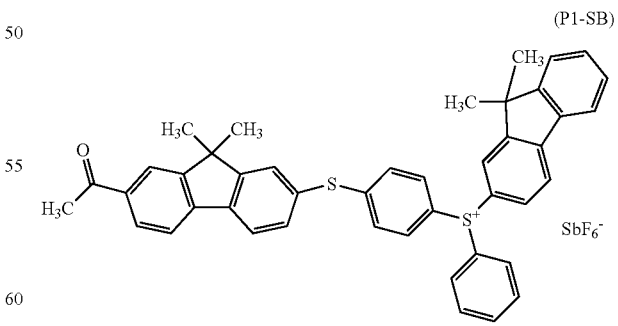

(P1-SB)

As in Example 2, 5.3 parts of P1-SB were obtained, except that 3.8 parts of potassium tris(pentafluoroethyl) trifluorophosphate in Example 2 were replaced with 3.7 parts of potassium hexafluoroantimonate. The product was identified by $^1$H-NMR and $^{19}$F-NMR.

[Example 5] Synthesis of {4-[2-(7-acetyl-9,9-dimethylfluorenyl)thio]phenyl}[2-(9,9-dimethylfluorenyl)]phenylsulfonium tetrakis(pentafluorophenyl) gallate (P1-GA)

[Chemical Formula 13]

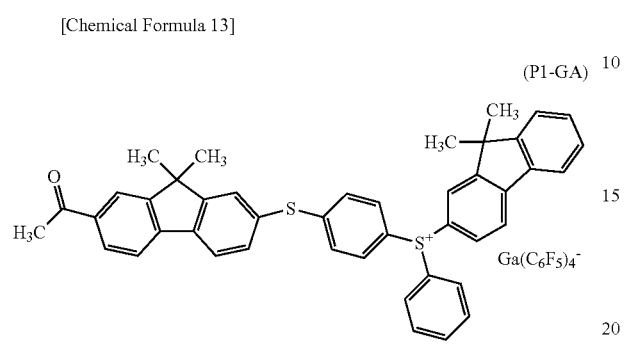

As in Example 2, 8.4 parts of P1-GA were obtained, except that 3.8 parts of potassium tris(pentafluoroethyl) trifluorophosphate in Example 2 were replaced with 5.4 parts of sodium tetrakis(pentafluorophenyl) gallate. The product was identified by $^1$H-NMR and $^{19}$F-NMR.

[Example 6] Synthesis of {4-[2-(7-acetyl-9,9-dimethylfluorenyl)thio]phenyl}[2-(9,9-dimethylfluorenyl)]phenylsulfonium hexafluorophosphate (P1-P)

[Chemical Formula 14]

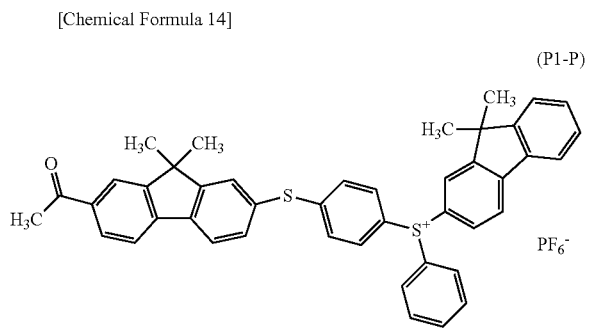

As in Example 2, 4.8 parts of P1-P were obtained, except that 3.8 parts of potassium tris(pentafluoroethyl) trifluorophosphate in Example 2 were replaced with 1.3 parts of potassium hexafluorophosphate. The product was identified by $^1$H-NMR and $^{19}$F-NMR.

[Example 7] Synthesis of {4-[2-(7-acetyl-9,9-dimethylfluorenyl)thio]phenyl}[2-(9,9-dimethylfluorenyl)]phenylsulfonium nonafluorobutanesulfonate (P1-NF)

[Chemical Formula 15]

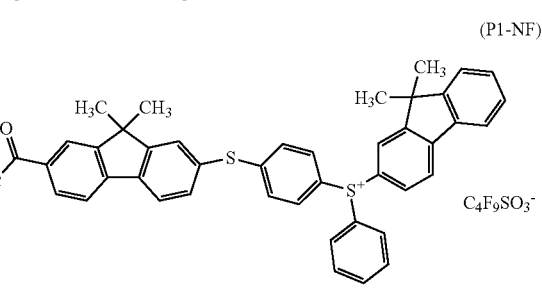

As in Example 2, 5.7 parts of P1-NF were obtained, except that 3.8 parts of potassium tris(pentafluoroethyl) trifluorophosphate in Example 2 were replaced with 2.4 parts of potassium nonafluorobutanesulfonate. The product was identified by $^1$H-NMR and $^{19}$F-NMR.

[Example 8] Synthesis of {4-[2-(7-acetyl-9,9-dimethylfluorenyl)thio]phenyl}[2-(9,9-dimethylfluorenyl)]phenylsulfonium trifluoromethanesulfonate (P1-TF)

[Chemical Formula 16]

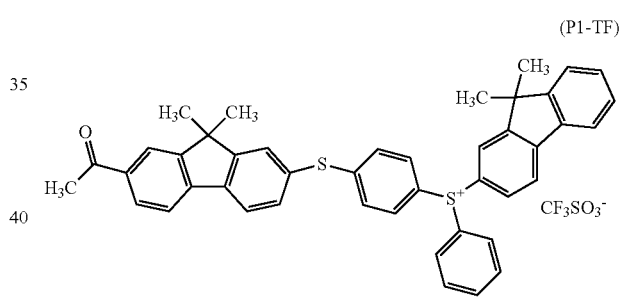

As in Example 2, 4.8 parts of P1-TF were obtained, except that 3.8 parts of potassium tris(pentafluoroethyl) trifluorophosphate in Example 2 were replaced with 1.3 parts of potassium trifluoromethanesulfonate. The product was identified by $^1$H-NMR and $^{19}$F-NMR.

[Example 9] Synthesis of {4-[2-(7-acetyl-9,9-dimethylfluorenyl)thio]phenyl}[2-(9,9-dimethylfluorenyl)]phenylsulfonium camphorsulfonate (P1-CS)

[Chemical Formula 17]

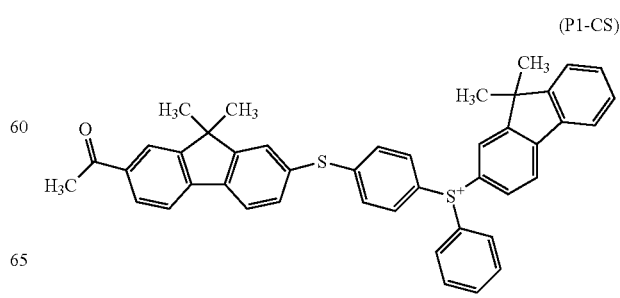

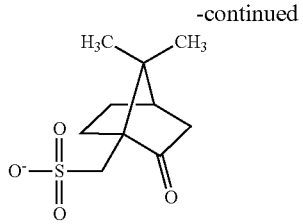

As in Example 2, 5.3 parts of P1-CS were obtained, except that 3.8 parts of potassium tris(pentafluoroethyl)trifluorophosphate in Example 2 were replaced with 1.8 parts of sodium camphorsulfonate. The product was identified by $^1$H-NMR.

[Example 10] Synthesis of {4-[2-(7-acetyl-9,9-dimethylfluorenyl)thio]phenyl}[2-(9,9-dimethylfluorenyl)]phenylsulfonium p-toluenesulfonate (P1-TS)

[Chemical Formula 18]

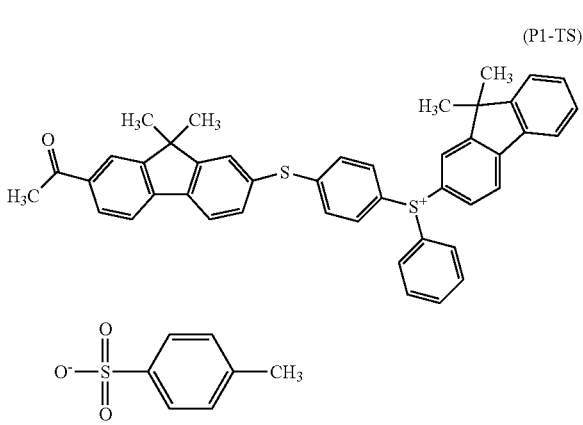

(P1-TS)

As in Example 2, 5.0 parts of P1-TS were obtained, except that 3.8 parts of potassium tris(pentafluoroethyl)trifluorophosphate in Example 2 were replaced with 1.4 parts of sodium p-toluenesulfonate. The product was identified by $^1$H-NMR.

[Example 11] Synthesis of {4-[2-(7-benzoyl-9,9-dimethylfluorenyl)thio]phenyl}[2-(9,9-dimethylfluorenyl)]phenylsulfonium methanesulfonate (P2-MS)

[Chemical Formula 19]

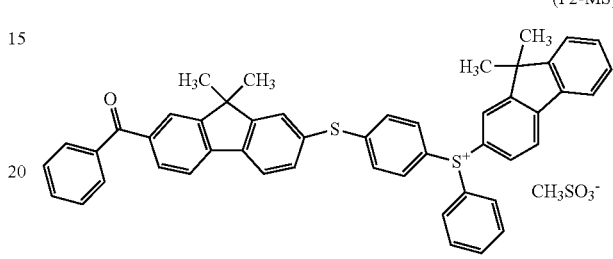

(P2-MS)

Mixed were 9.1 parts of benzoyl cloride, 10.3 parts of aluminum cloride and 18.2 parts of dichloromethane, and cooled to 5° C. under stirring. Into the solution, a mixture solution of 10.0 parts of {4-[2-(9,9-dimethylfluorenyl)thio]phenyl}[2-(9,9-dimethylfluorenyl)]phenylsulfonium methanesulfonate and 18.2 parts of dichloromethane were added dropwise slowly. After allowing to react for one hour, the reaction solution was added dropwise into 75 parts of water. Then, the solution was stirred for 30 minutes, and operated to stand for 30 minutes. The water layer was removed, then, 75 parts of water were added into the organic layer, and the solution was stirred and washed. After washing five times in total, the organic layer was transferred to a rotary evaporator, and the solvent was removed by distillation, so that P2-MS was obtained as a yellow powder in a yield of 80%. The product was identified by $^1$H-NMR.

[Example 12] Synthesis of {4-[2-(7-benzoyl-9,9-dimethylfluorenyl)thio]phenyl}[2-(9,9-dimethylfluorenyl)]phenylsulfonium tris(pentafluoroethyl)trifluorophosphate (P2-FP)

[Chemical Formula 20]

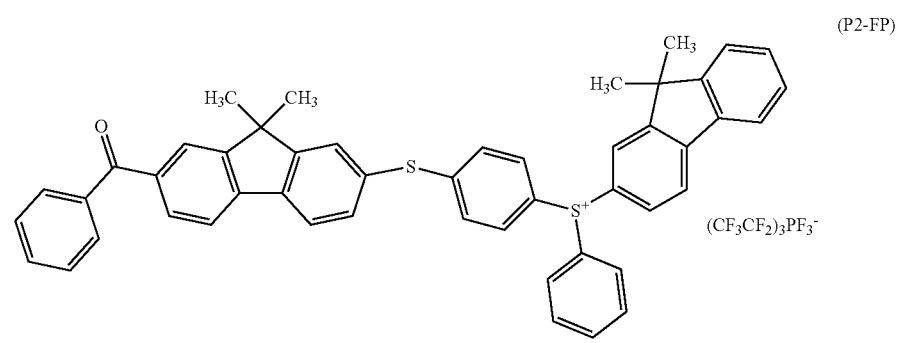

(P2-FP)

Dissolved were 5.0 parts of {4-[2-(7-benzoyl-9,9-dimethylfluorenyl)thio]phenyl}[2-(9,9-dimethylfluorenyl)thio]phenylsulfonium methanesulfonate (P2-MS) synthesized in Example 11 in 31.7 parts of dichloromethane. Into the solution, 3.2 parts of potassium tris(pentafluoroethyl)trifluorophosphate and 28 parts of deionized water were added, and stirred for one hour at room temperature. The organic layer was washed with 28 parts of deionized water five times. The organic layer was transferred to a rotary evaporator, and the solvent was removed by distillation, so that 6.4 parts of P2-FP were obtained as a pale yellow solid in a yield of 90%. The product was identified by $^1$H-NMR and $^{19}$F-NMR.

[Example 13] Synthesis of {4-[2-(7-benzoyl-9,9-dimethylfluorenyl)thio]phenyl}[2-(9,9-dimethylfluorenyl)]phenylsulfonium tetrakis(pentafluorophenyl)borate (P2-B)

[Chemical Formula 21]

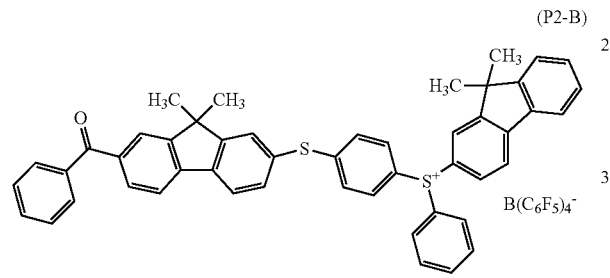

As in Example 12, 7.7 parts of P2-B were obtained, except that 3.2 parts of potassium tris(pentafluoroethyl)trifluorophosphate in Example 12 were replaced with 4.6 parts of sodium tetrakis(pentafluorophenyl)borate. The product was identified by $^1$H-NMR and $^{19}$F-NMR.

[Example 14] Synthesis of {4-[2-(7-benzoyl-9,9-dimethylfluorenyl)thio]phenyl}[2-(9,9-dimethylfluorenyl)]phenylsulfonium hexafluoroantimonate (P2-SB)

[Chemical Formula 22]

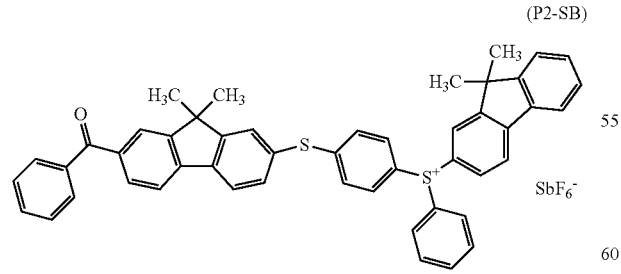

As in Example 12, 5.3 parts of P2-SB were obtained, except that 3.2 parts of potassium tris(pentafluoroethyl)trifluorophosphate in Example 12 were replaced with 3.45 parts of potassium hexafluoroantimonate. The product was identified by $^1$H-NMR and $^{19}$F-NMR.

[Example 15] Synthesis of {4-[2-(7-benzoyl-9,9-dimethylfluorenyl)thio]phenyl}[2-(9,9-dimethylfluorenyl)]phenylsulfonium tetrakis(pentafluorophenyl)gallate (P2-GA)

[Chemical Formula 23]

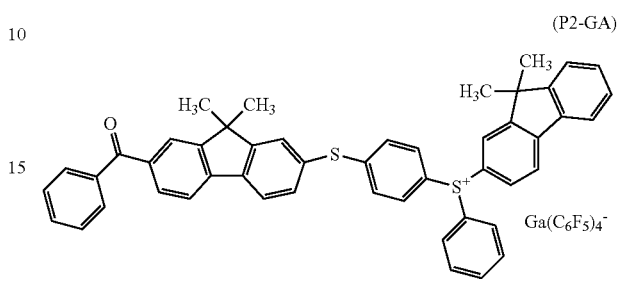

As in Example 12, 8.1 parts of P2-GA were obtained, except that 3.2 parts of potassium tris(pentafluoroethyl)trifluorophosphate in Example 12 were replaced with 5.0 parts of sodium tetrakis(pentafluorophenyl)gallate. The product was identified by $^1$H-NMR and $^{19}$F-NMR.

[Example 16] Synthesis of {4-[2-(7-benzoyl-9,9-dimethylfluorenyl)thio]phenyl}[2-(9,9-dimethylfluorenyl)]phenylsulfonium hexafluorophosphate (P2-P)

[Chemical Formula 24]

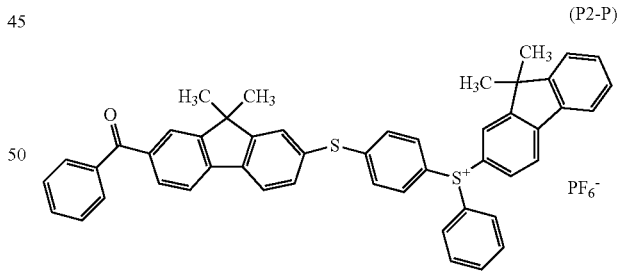

As in Example 12, 4.7 parts of P2-P were obtained, except that 3.2 parts of potassium tris(pentafluoroethyl)trifluorophosphate in Example 12 were replaced with 1.2 parts of potassium hexafluorophosphate. The product was identified by $^1$H-NMR and $^{19}$F-NMR.

[Example 17] Synthesis of {4-[2-(7-benzoyl-9,9-dimethylfluorenyl)thio]phenyl}[2-(9,9-dimethylfluorenyl)]phenylsulfonium nonafluorobutanesulfonate (P2-NF)

[Chemical Formula 25]

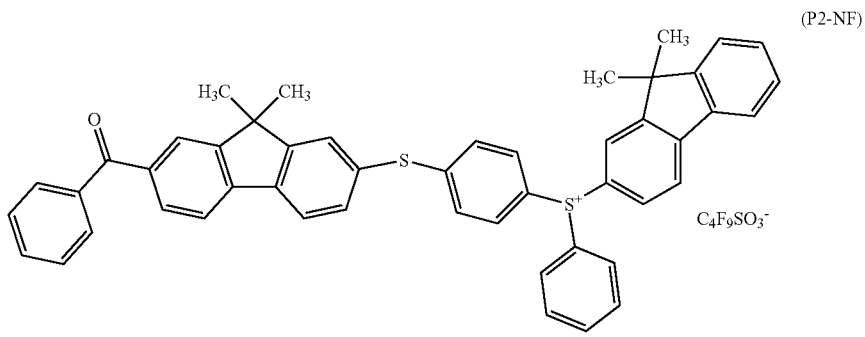

As in Example 12, 5.6 parts of P2-NE were obtained, except that 3.2 parts of potassium tris(pentafluoroethyl)trifluorophosphate in Example 12 were replaced with 2.2 parts of potassium nonafluorobutanesulfonate. The product was identified by $^1$H-NMR and $^{19}$F-NMR.

[Example 18] Synthesis of {4-[2-(7-benzoyl-9,9-dimethylfluorenyl)thio]phenyl}[2-(9,9-dimethylfluorenyl)]phenylsulfonium trifluoromethanesulfonate (P2-TF)

[Chemical Formula 26]

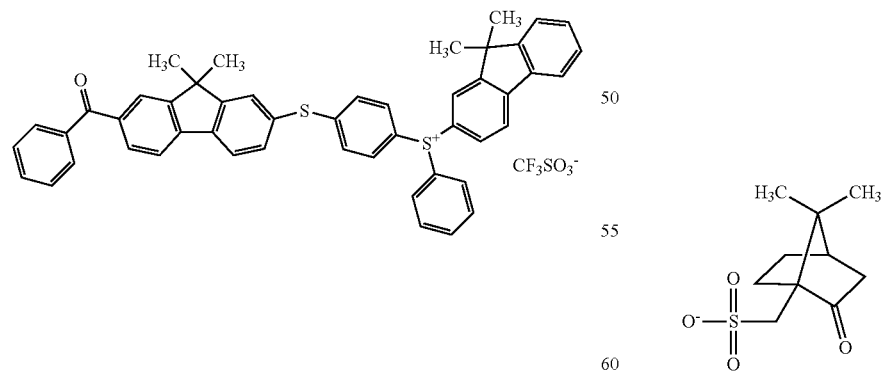

As in Example 12, 4.8 parts of P2-TF were obtained, except that 3.2 parts of potassium tris(pentafluoroethyl)trifluorophosphate in Example 12 were replaced with 1.2 parts of potassium trifluorometanesulfonate. The product was identified by $^1$H-NMR and $^{19}$F-NMR.

[Example 19] Synthesis of {4-[2-(7-benzoyl-9,9-dimethylfluorenyl)thio]phenyl}[2-(9,9-dimethylfluorenyl)]phenylsulfonium camphorsulfonate (P2-CS)

[Chemical Formula 27]

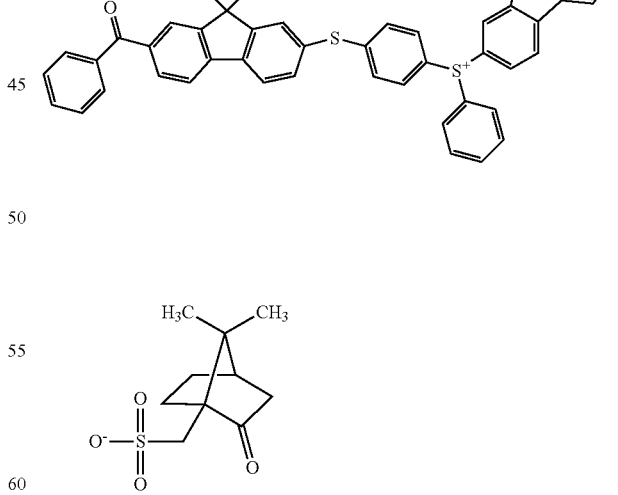

As in Example 12, 5.2 parts of P2-CS were obtained, except that 3.2 parts of potassium tris(pentafluoroethyl)trifluorophosphate in Example 12 were replaced with 1.7 parts of sodium camphorsulfonate. The product was identified by $^1$H-NMR.

[Example 20] Synthesis of {4-[2-(7-benzoyl-9,9-dimethylfluorenyl)thio]phenyl}[2-(9,9-dimethylfluorenyl)]phenylsulfonium p-toluenesulfonate (P2-TS)

[Chemical Formula 28]

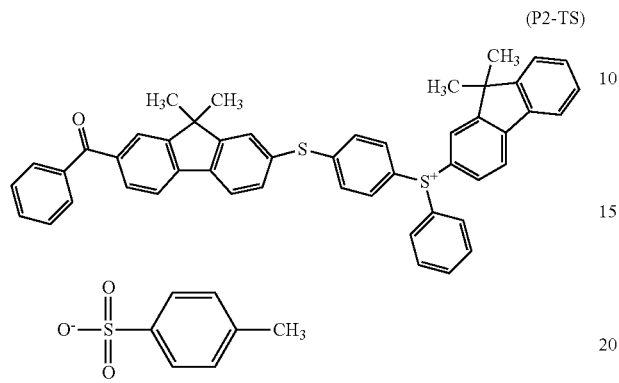

As in Example 12, 4.9 parts of P2-TS were obtained, except that 3.2 parts of potassium tris(pentafluoroethyl)trifluorophosphate in Example 12 were replaced with 1.3 parts of sodium p-toluenesulfonate. The product was identified by $^1$H-NMR.

[Example 21] Synthesis of {4-[2-(7-valeryl-9,9-dimethylfluorenyl)thio]phenyl}[2-(9,9-dimethylfluorenyl)]phenylsulfonium tris(pentafluoroethyl)trifluorophosphate (P3-FP)

[Chemical Formula 29]

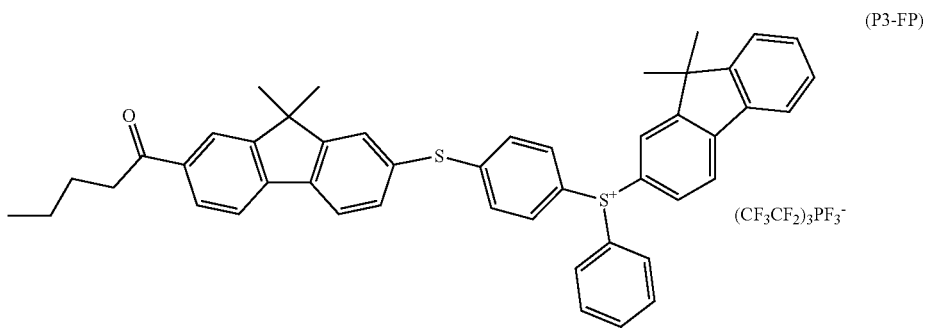

Mixed were 10.1 parts of valeryl cloride, 12.1 parts of aluminum cloride and 15.1 parts of dichloromethane, and cooled to 5° C. under stirring. Into the solution, a mixture solution of 10.0 parts of {4-[2-(9,9-dimethylfluorenyl)thio]phenyl}[2-(9,9-dimethylfluorenyl)]phenylsulfonium methanesulfonate and 15.1 parts of dichloromethane were added dropwise slowly. After allowing to react for one hour, the reaction solution was added dropwise into 75 parts of water. Then, the solution was stirred for 30 minutes, and operated to stand for 30 minutes. Into the solution, 7.0 parts of potassium tris(pentafluoroethyl)trifluorophosphate and 75 parts of deionized water were added, and stirred for one hour at room temperature. Then, the solution was operated to stand for 30 minutes. The water layer was removed, then, 75 parts of water were added into the organic layer, and the solution was stirred and washed. After washing five times in total, the organic layer was transferred to a rotary evaporator, and the solvent was removed by distillation, so that P3-FP was obtained as a yellow powder in a yield of 70%. The product was identified by $^1$H-NMR and $^{19}$F-NMR.

[Example 22] Synthesis of {4-[2-(7-naphthoyl-9,9-dimethylfluorenyl)thio]phenyl}[2-(9,9-dimethylfluorenyl)]phenylsulfonium tris(pentafluoroethyl)trifluorophosphate (P4-FP)

[Chemical Formula 30]

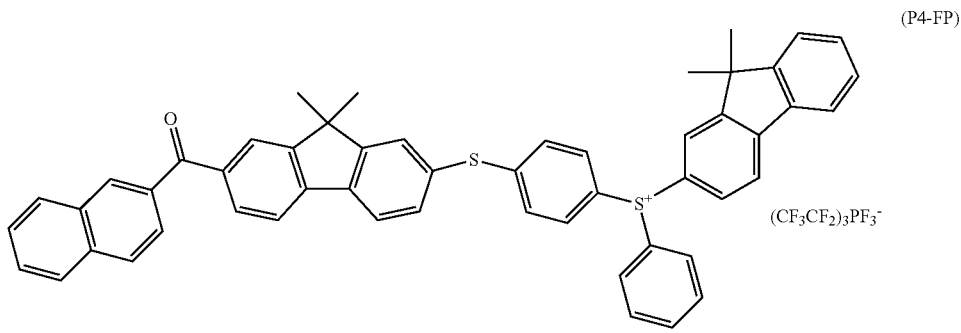

As in Example 21, P4-FP was obtained as a yellow powder in a yield of 75%, except that 10.1 parts of valeryl chloride in Example 21 were replaced with 15.2 parts of naphthoyl chloride. The product was identified by $^1$H-NMR and $^{19}$F-NMR.

[Example 23] Synthesis of {3-methyl-4-[2-(7-acetyl-9,9-dimethylfluorenyl)thio]phenyl}[2-(9,9-dimethylfluorenyl)](2-methylphenyl)sulfonium tris(pentafluoroethyl)trifluorophosphate (P5-FP)

[Chemical Formula 31]

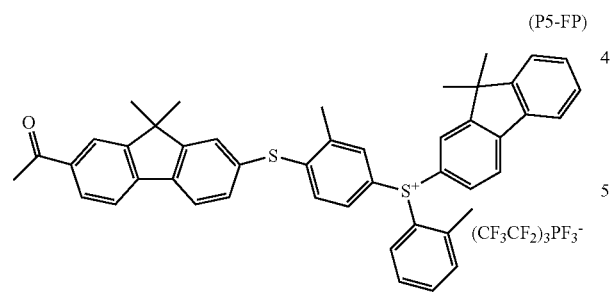

Mixed were 7.6 parts of acethyl cloride, 15.5 parts of aluminum cloride and 27.3 parts of dichloromethane, and cooled to 5° C. under stirring. Into the solution, a mixture solution of 14.5 parts of {3-methyl-4-[2-(9,9-dimethylfluorenyl)thio]phenyl}[2-(9,9-dimethylfluorenyl)](2-methylphenyl)sulfonium methanesulfonate and 27.3 parts of dichloromethane were added dropwise slowly. After allowing to react for one hour, the reaction solution was added dropwise into 100 parts of water. Then, the solution was stirred for 30 minutes, and operated to stand for 30 minutes. Into the solution, 10.0 parts of potassium tris(pentafluoroethyl)trifluorophosphate and 100 parts of deionized water were added, and stirred for one hour at room temperature. Then, the water layer was removed, then, 100 parts of water were added into the organic layer, and the solution was stirred and washed. After washing five times in total, the organic layer was transferred to a rotary evaporator, and the solvent was removed by distillation, so that P5-FP was obtained as a yellow powder in a yield of 80%. The product was identified by $^1$H-NMR and $^{19}$F-NMR.

[Example 24] Synthesis of {3-methyl-4-[2-(7-benzoyl-9,9-dimethylfluorenyl)thio]phenyl}[2-(9,9-dimethylfluorenyl)](2-methylphenyl)sulfonium tris(pentafluoroethyl)trifluorophosphate (P6-FP)

[Chemical Formula 32]

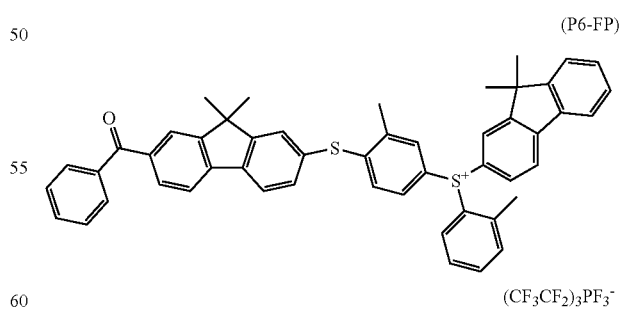

As in Example 23, P6-FP was obtained as a yellow powder in a yield of 80%, except that 7.6 parts of acetyl chloride in Example 23 were replaced with 10.2 parts of benzoyl chloride. The product was identified by $^1$H-NMR and $^{19}$F-NMR.

[Example 25] Synthesis of {2,5-dimethyl-4-[2-(7-acetyl-9,9-dimethylfluorenyl)thio]phenyl}[2-(9,9-dimethylfluorenyl)](2,5-dimethylphenyl)sulfonium tris(pentafluoroethyl)trifluorophosphate (P7-FP)

[Chemical Formula 33]

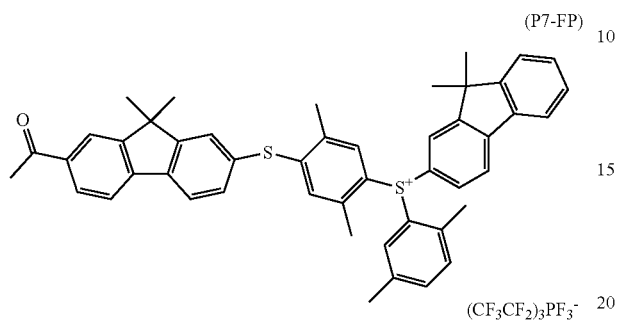

(P7-FP)

$(CF_3CF_2)_3PF_3^-$

As in Example 23, P7-FP was obtained as a yellow powder in a yield of 80%, except that 14.5 parts of "{3-methyl-4-[2-(9,9-dimethylfluorenyl)thio]phenyl}[2-(9,9-dimethylfluorenyl)](2-methylphenyl)sulfonium methanesulfonate" in Example 23 were replaced with 14.0 parts of "{2,5-dimethyl-4-[2-(9,9-dimethylfluorenyl)thio]phenyl}[2-(9,9-dimethylfluorenyl)](2,5-dimethylphenyl)sulfonium methanesulfonate". The product was identified by $^1$H-NMR and $^{19}$F-NMR.

[Example 26] Synthesis of {2,5-dimethyl-4-[2-(7-benzoyl-9,9-dimethylfluorenyl)thio]phenyl}[2-(9,9-dimethylfluorenyl)](2,5-dimethylphenyl)sulfonium tris(pentafluoroethyl)trifluorophosphate (P8-FP)

[Chemical Formula 34]

As in Example 25, P8-FP was obtained as a yellow powder in a yield of 80%, except that 7.6 parts of acetyl chloride in Example 25 were replaced with 10.2 parts of benzoyl chloride. The product was identified by $^1$H-NMR and $^{19}$F-NMR.

[Example 27] Synthesis of {3-methoxy-4-[2-(7-acetyl-9,9-dimethylfluorenyl)thio]phenyl}[2-(9,9-dimethylfluorenyl)](2-methoxyphenyl)sulfonium tris(pentafluoroethyl)trifluorophosphate (P9-FP)

[Chemical Formula 35]

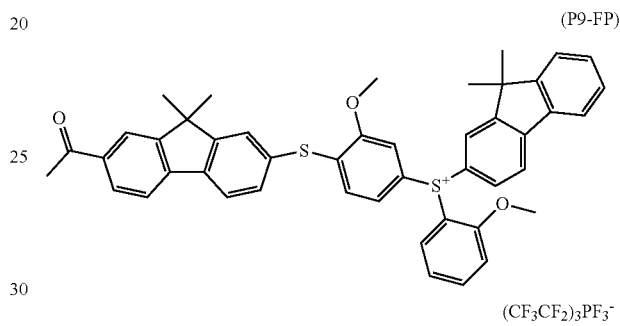

(P9-FP)

$(CF_3CF_2)_3PF_3^-$

As in Example 23, P9-FP was obtained as a yellow powder in a yield of 80%, except that 14.5 parts of "{3-methyl-4-[2-(9,9-dimethylfluorenyl)thio]phenyl}[2-(9,9-dimethylfluorenyl)](2-methylphenyl)sulfonium methanesulfonate" in Example 23 were replaced with 14.5 parts of "{3-methoxy-4-[2-(9,9-dimethylfluorenyl)thio]phenyl}[2-(9,9-dimethylfluorenyl)](2-methoxyphenyl)sulfonium methanesulfonate". The product was identified by $^1$H-NMR and $^{19}$F-NMR.

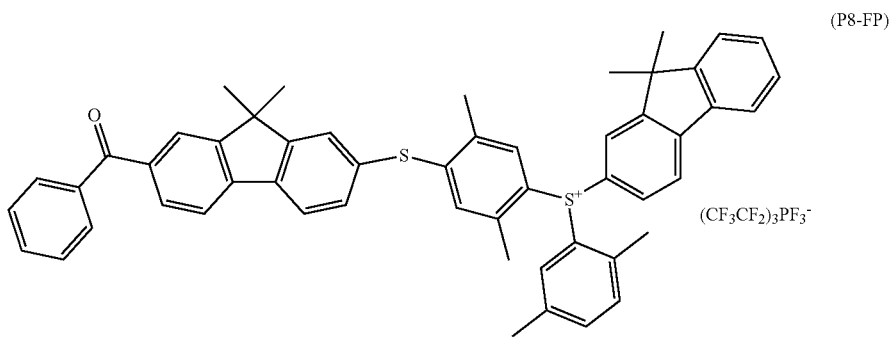

(P8-FP)

$(CF_3CF_2)_3PF_3^-$

[Example 28] Synthesis of {3-methoxy-4-[2-(7-benzoyl-9,9-dimethylfluorenyl)thio]phenyl}[2-(9,9-dimethylfluorenyl)](2-methoxylphenyl)sulfonium tris(pentafluoroethyl)trifluorophosphate (P10-FP)

[Chemical Formula 36]

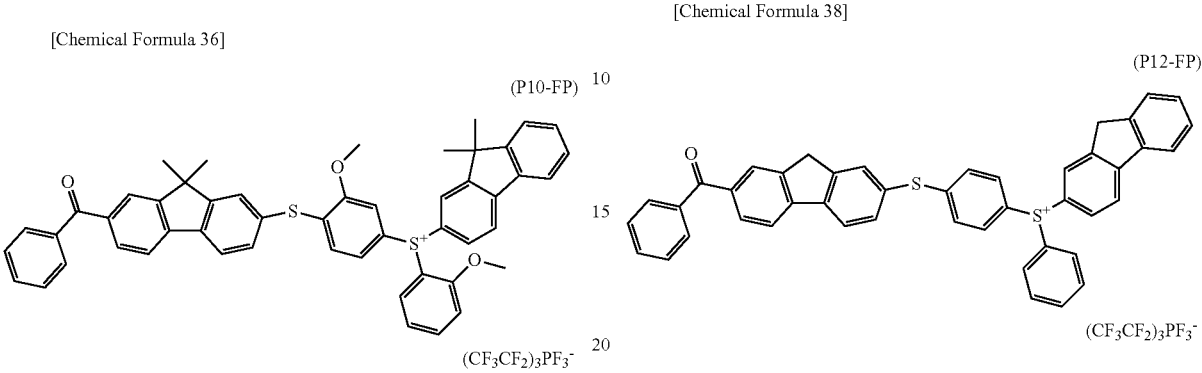

(P10-FP)

(CF₃CF₂)₃PF₃⁻

As in Example 27, P10-FP was obtained as a yellow powder in a yield of 80%, except that 7.6 parts of acetyl chloride in Example 27 were replaced with 10.2 parts of benzoyl chloride. The product was identified by ¹H-NMR and ¹⁹F-NMR.

[Example 29] Synthesis of {4-[2-(7-acetylfluorenyl)thio]phenyl}(2-fluorenyl)phenylsulfonium tris(pentafluoroethyl)trifluorophosphate (P11-FP)

[Chemical Formula 37]

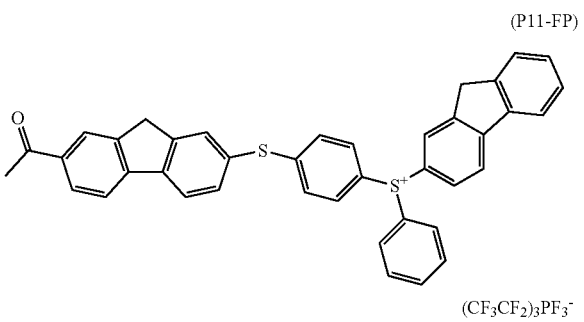

(P11-FP)

(CF₃CF₂)₃PF₃⁻

As in Example 23, P11-FP was obtained as a yellow powder in a yield of 80%, except that 14.5 parts of "{3-methyl-4-[2-(9,9-dimethylfluorenyl)thio]phenyl}[2-(9,9-dimethylfluorenyl)](2-methylphenyl)sulfonium methanesulfonate" in Example 23 were replaced with 15.5 parts of "{4-(2-fluorenyl)thiophenyl}(2-fluorenyl)phenylsulfonium methanesulfonate". The product was identified by ¹H-NMR and ¹⁹F-NMR.

[Example 30] Synthesis of {4-[2-(7-benzoylfluorenyl)thio]phenyl}(2-fluorenyl)phenylsulfonium tris(pentafluoroethyl)trifluorophosphate (P12-FP)

[Chemical Formula 38]

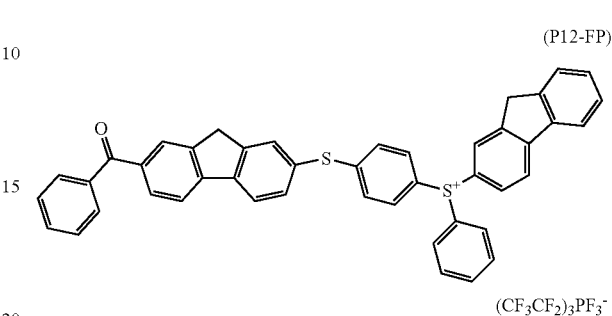

(P12-FP)

(CF₃CF₂)₃PF₃⁻

As in Example 29, P12-FP was obtained as a yellow powder in a yield of 80%, except that 7.6 parts of acetyl chloride in Example 29 were replaced with 10.2 parts of benzoyl chloride. The product was identified by ¹H-NMR and ¹⁹F-NMR.

[Example 31] Synthesis of {4-[2-(7-acetyl-9,9-diphenylfluorenyl)thio]phenyl}[2-(9,9-diphenylfluorenyl)]phenylsulfonium tris(pentafluoroethyl)trifluorophosphate (P13-FP)

[Chemical Formula 39]

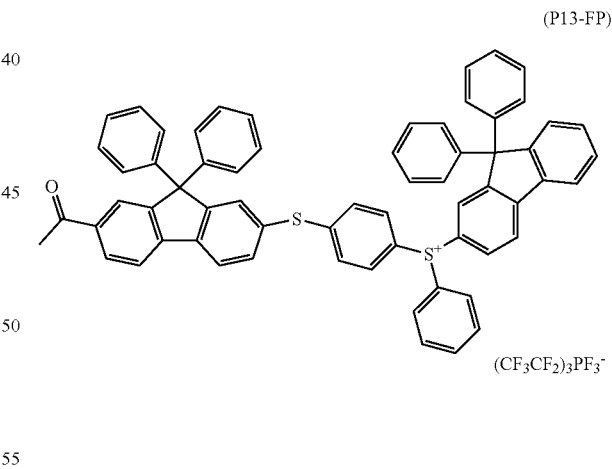

(P13-FP)

(CF₃CF₂)₃PF₃⁻

As in Example 23, P13-FP was obtained as a yellow powder in a yield of 80%, except that 14.5 parts of "{3-methyl-4-[2-(9,9-dimethylfluorenyl)thio]phenyl}[2-(9,9-dimethylfluorenyl)](2-methylphenyl)sulfonium methanesulfonate" in Example 23 were replaced with 14.5 parts of "{4-[2-(9,9-diphenylfluorenyl)thio]phenyl}[2-(9,9-diphenylfluorenyl)]phenylsulfonium methanesulfonate". The product was identified by ¹H-NMR and ¹⁹F-NMR.

[Example 32] Synthesis of {4-[2-(7-benzoyl-9,9-diphenylfluorenyl)thio]phenyl}[2-(9,9-diphenylfluorenyl)]phenylsulfonium tris(pentafluoroethyl)trifluorophosphate (P14-FP)

[Chemical Formula 40]

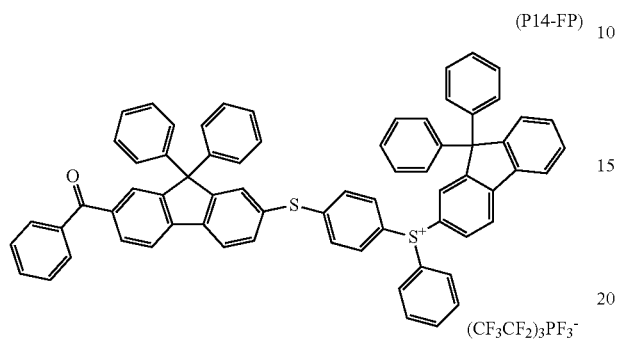

(P14-FP)

(CF$_3$CF$_2$)$_3$PF$_3^-$

As in Example 31, P14-FP was obtained as a yellow powder in a yield of 80%, except that 7.6 parts of acetyl chloride in Example 31 were replaced with 10.2 parts of benzoyl chloride. The product was identified by $^1$H-NMR and $^{19}$F-NMR.

[Comparative Example 1] Synthesis of Compound H-1

[Chemical Formula 41]

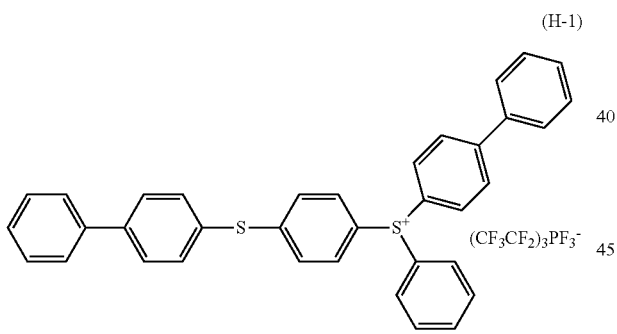

(H-1)

(CF$_3$CF$_2$)$_3$PF$_3^-$

Uniformly mixed were 1.0 parts of 4-[(phenyl) sulfinyl]biphenyl, 1.1 parts of 4-(phenylthio)biphenyl, 2.2 parts of acetic anhydride and 1.73 parts of methanesulfonic acid, and allowed to react at 65° C. for 3 hours. Subsequently, the reaction solution was cooled to room temperature (about 25° C.) and poured into 5.0 parts of deionized water. The mixture was extracted with 5.0 parts of dichloromethane, and the dichloromethane layer was washed with water until the pH of the water layer became neutral. Thereto was added 10 parts of toluene, and the mixture was stirred. Subsequently, the operation of allowing the mixture to stand for 30 minutes and then removing the supernatant was performed twice to wash the product. The residue was dissolved with 10 parts of dichloromethane, and thereto were added 1.8 parts of potassium tris(pentafluoroethyl)trifluorophosphate and 10 parts of ion-exchange water. The solution was stirred at room temperature for one hour. After washing with 10 parts of deionized water five times, the organic layer was transferred to a rotary evaporator, and the solvent was removed by distillation, so that 2.8 parts of compound H-1 was obtained as a pale yellow viscous material in a yield of 90%. The product was identified by $^1$H-NMR and $^{19}$F-NMR.

[Comparative Example 2] Synthesis of Compound H-2

[Chemical Formula 42]

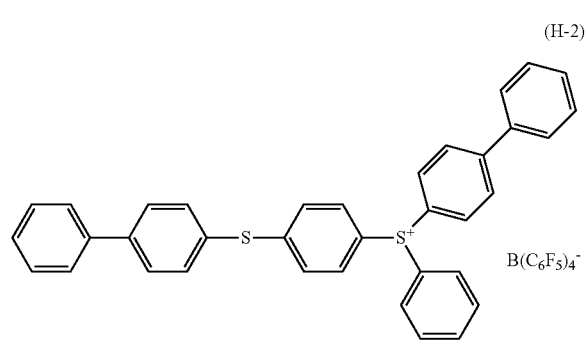

(H-2)

B(C$_6$F$_5$)$_4^-$

As in Comparative Example 1, 3.5 parts of compound H-2 was obtained, except that 1.8 parts of potassium tris(pentafluoroethyl)trifluorophosphate in Comparative Example 1 were replaced with 2.4 parts of lithium tetrakis(pentafluorophenyl)borate manufactured by Aldrich. The product was identified by $^1$H-NMR and $^{19}$F-NMR.

[Comparative Example 3] Synthesis of Compound H-3

[Chemical Formula 43]

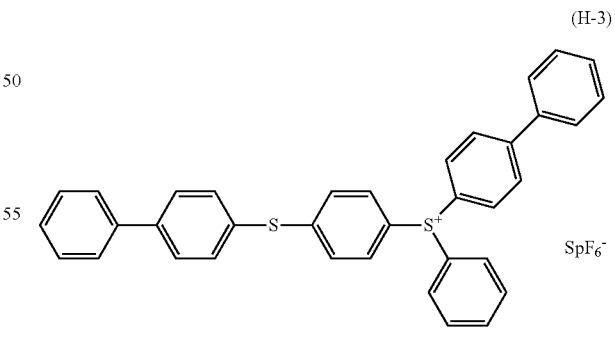

(H-3)

SpF$_6^-$

As in Comparative Example 1, 2.2 parts of compound H-3 was obtained, except that 1.8 parts of potassium tris(pentafluoroethyl)trifluorophosphate in Comparative Example 1 were replaced with 1.0 parts of potassium hexafluoroantimonate. The product was identified by $^1$H-NMR and $^{19}$F-NMR.

[Comparative Example 4] Synthesis of Compound H-4

[Chemical Formula 44]

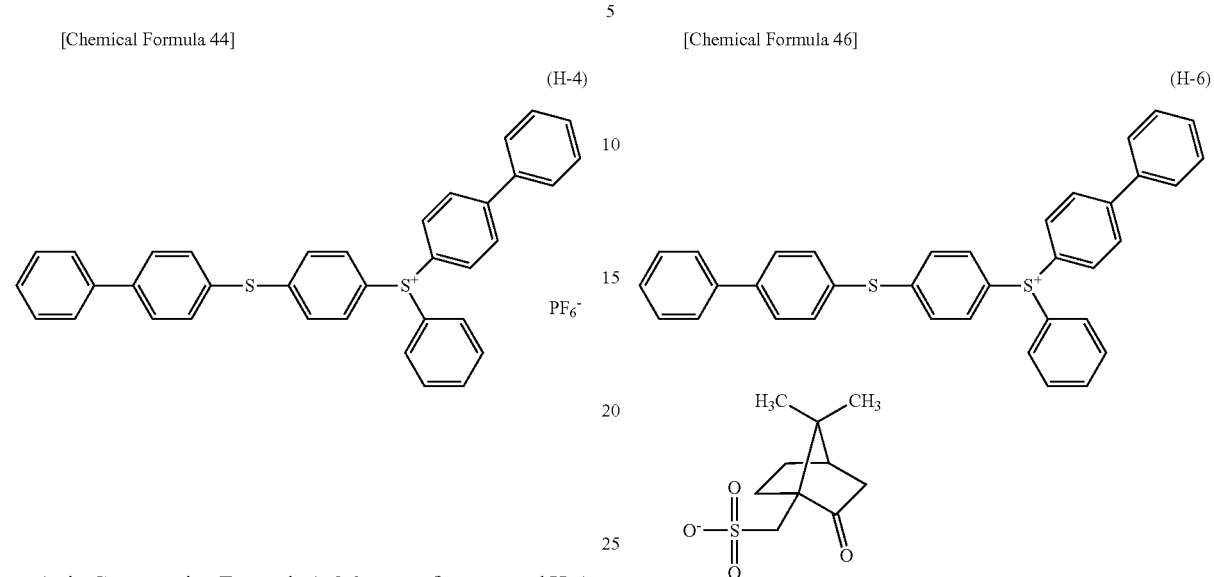

(H-4)

As in Comparative Example 1, 2.0 parts of compound H-4 was obtained, except that 1.8 parts of potassium tris(pentafluoroethyl)trifluorophosphate in Comparative Example 1 were replaced with 0.62 parts of potassium hexafluoroaphosphate. The product was identified by $^1$H-NMR and $^{19}$F-NMR.

[Comparative Example 5] Synthesis of Compound H-5

[Chemical Formula 45]

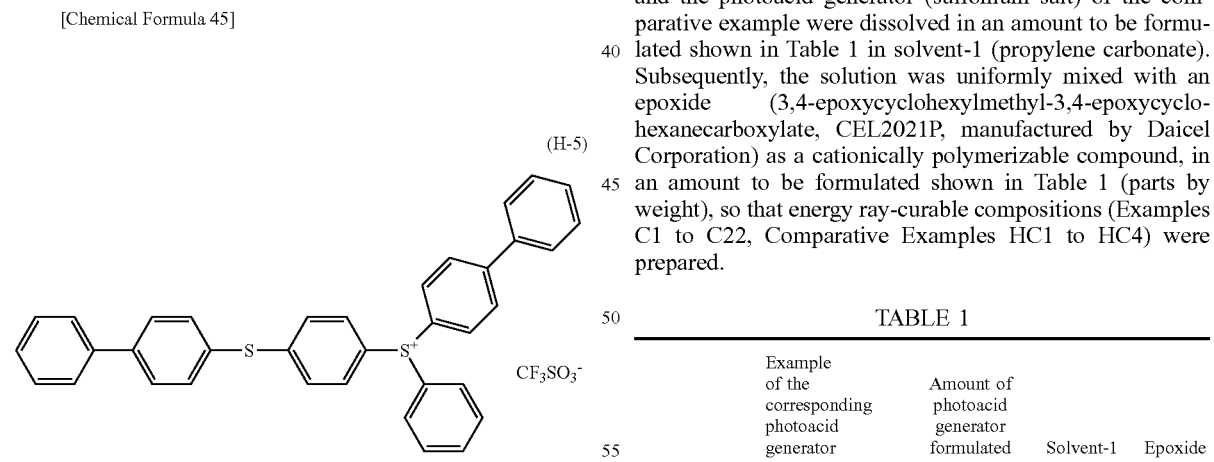

(H-5)

As in Comparative Example 1, 2.0 parts of compound H-5 was obtained, except that 1.8 parts of potassium tris(pentafluoroethyl)trifluorophosphate in Comparative Example 1 were replaced with 0.7 parts of potassium trifluorometanesulfonate. The product was identified by $^1$H-NMR and $^{19}$F-NMR.

[Comparative Example 6] Synthesis of Compound H-6

[Chemical Formula 46]

(H-6)

As in Comparative Example 1, 2.2 parts of compound H-6 was obtained, except that 1.8 parts of potassium tris(pentafluoroethyl)trifluorophosphate in Comparative Example 1 were replaced with 0.92 parts of potassium camphorsulfonate. The product was identified by $^1$H-NMR.

(Preparation and Evaluation of Energy Ray-Curable Compositions)

<Preparation of Curable Compositions>

The photoacid generator (sulfonium salt) of the invention and the photoacid generator (sulfonium salt) of the comparative example were dissolved in an amount to be formulated shown in Table 1 in solvent-1 (propylene carbonate). Subsequently, the solution was uniformly mixed with an epoxide (3,4-epoxycyclohexylmethyl-3,4-epoxycyclohexanecarboxylate, CEL2021P, manufactured by Daicel Corporation) as a cationically polymerizable compound, in an amount to be formulated shown in Table 1 (parts by weight), so that energy ray-curable compositions (Examples C1 to C22, Comparative Examples HC1 to HC4) were prepared.

TABLE 1

| Example | Example of the corresponding photoacid generator | Amount of photoacid generator formulated | Solvent-1 | Epoxide |
|---|---|---|---|---|
| C1 | Example 2 | 0.25 | 0.25 | 100 |
| C2 | Example 3 | 0.25 | 0.25 | 100 |
| C3 | Example 4 | 0.25 | 0.25 | 100 |
| C4 | Example 5 | 0.25 | 0.25 | 100 |
| C5 | Example 6 | 1.25 | 1.25 | 100 |
| C6 | Example 12 | 0.25 | 0.25 | 100 |
| C7 | Example 13 | 0.25 | 0.25 | 100 |
| C8 | Example 14 | 0.25 | 0.25 | 100 |
| C9 | Example 15 | 0.25 | 0.25 | 100 |
| C10 | Example 16 | 1.25 | 1.25 | 100 |
| C11 | Example 21 | 0.25 | 0.25 | 100 |

TABLE 1-continued

| | Example of the corresponding photoacid generator | Amount of photoacid generator formulated | Solvent-1 | Epoxide |
|---|---|---|---|---|
| C12 | Example 22 | 0.25 | 0.25 | 100 |
| C13 | Example 23 | 0.25 | 0.25 | 100 |
| C14 | Example 24 | 0.25 | 0.25 | 100 |
| C15 | Example 25 | 0.25 | 0.25 | 100 |
| C16 | Example 26 | 0.25 | 0.25 | 100 |
| C17 | Example 27 | 0.25 | 0.25 | 100 |
| C18 | Example 28 | 0.25 | 0.25 | 100 |
| C19 | Example 29 | 0.25 | 0.25 | 100 |
| C20 | Example 30 | 0.25 | 0.25 | 100 |
| C21 | Example 31 | 0.25 | 0.25 | 100 |
| C22 | Example 32 | 0.25 | 0.25 | 100 |
| Comparative Example | | | | |
| HC1 | C.Example 1 | 0.25 | 0.25 | 100 |
| HC2 | C.Example 2 | 0.25 | 0.25 | 100 |
| HC3 | C.Example 3 | 0.25 | 0.25 | 100 |
| HC4 | C.Example 4 | 1.25 | 1.25 | 100 |

The sulfonium salt obtained in Example 6, 16 or Comparative Example 4 was formulated in a relatively large amount, because it was a hexafluorophosphate and therefore the acid generated therefrom had a weak strength as compared with that generated from tris(pentafluoroethyl)trifluorophosphate, tetrakis(pentafluorophenyl)borate, hexafluoroantimonate, or tetrakis(pentafluorophenyl)garate obtained in one of Examples 2 to 5, 12 to 15, 21 to 32 or Comparative Examples 1 to 3, and had low activity for cationic polymerization. According to this, the solvent was also formulated in a relatively large amount.

<Evaluation of Photosensitivity (Photo-Curability)>

The energy ray-curable composition obtained above was applied to a polyethylene terephthalate (PET) film using an applicator (40 μm). Using an ultraviolet irradiator, the PET film was irradiated with ultraviolet light whose wavelength was restricted with filters. The filters used was IRCF02 Filter (manufactured by EYE GRAPHICS Co., Ltd., a filter for cutting off light with wavelengths of less than 340 nm). Forty minutes after the irradiation, the pencil hardness (JIS K 5600-5-4: 1999) of the coating film hardness was measured and evaluated according to the criteria below (the coating film had a thickness of about 40 μm after the curing). The results were shown in Table 2. The higher pencil hardness indicates that the photo-curability of the energy ray-curable composition is better, namely, the ability of the sulfonium salt to initiate polymerization of the cationically polymerizable compound (the photosensitivity of the sulfonium salt) is excellent.

(Evaluation Criteria)
⊙: The pencil hardness is 2H or higher.
○: The pencil hardness is from H to B.
Δ: The pencil hardness is from 2B to 4B.
x: Due to liquidness or tackiness, it is not possible to measure the pencil hardness.

(Ultraviolet Light Irradiation Conditions)
Ultraviolet ray irradiator: belt conveyor-type UV irradiator (manufactured by EYE GRAPHICS Co., Ltd.)
Lamp: 1.5 kW high-pressure mercury lamp
Filters: IRCF02 Filter (manufactured by EYE GRAPHICS Co; Ltd.)
Irradiance (measured with a 365 nm head photometer): 145 mW/cm$^2$ Integral light dose (measured with a 365 nm head photometer):
condition-1, 50 mJ/cm$^2$
condition-2, 100 mJ/cm$^2$
condition-3, 200 mJ/cm$^2$ <Storage Stability>

The energy ray-curable composition obtained above was heated at 80° C. under shading and stored for one month. The viscosity of the formulation sample was measured before and after the heating and evaluated according to the criteria below. The less increase in the viscosity, the better the storage stability.

(Evaluation Criteria)
x: After the heating, the viscosity is changed by 1.5 times or more.
○: After the heating, the viscosity is changed by less than 1.5 times.

TABLE 2

| | Photo-curability | | | Storage stability |
|---|---|---|---|---|
| | Condition-1 | Condition-2 | Condition-3 | |
| Example | | | | |
| C1 | ○ | ○ | ⊙ | ○ |
| C2 | ○ | ○ | ⊙ | ○ |
| C3 | ○ | ○ | ⊙ | ○ |
| C4 | ○ | ○ | ⊙ | ○ |
| C5 | ○ | ○ | ⊙ | ○ |
| C6 | ○ | ○ | ⊙ | ○ |
| C7 | ○ | ○ | ⊙ | ○ |
| C8 | ○ | ○ | ⊙ | ○ |
| C9 | ○ | ○ | ⊙ | ○ |
| C10 | ○ | ○ | ⊙ | ○ |
| C11 | ○ | ○ | ⊙ | ○ |
| C12 | ○ | ○ | ⊙ | ○ |
| C13 | ○ | ○ | ⊙ | ○ |
| C14 | ○ | ○ | ⊙ | ○ |
| C15 | ○ | ○ | ⊙ | ○ |
| C16 | ○ | ○ | ⊙ | ○ |
| C17 | ○ | ○ | ⊙ | ○ |
| C18 | ○ | ○ | ⊙ | ○ |
| C19 | ○ | ○ | ⊙ | ○ |
| C20 | ○ | ○ | ⊙ | ○ |
| C21 | ○ | ○ | ⊙ | ○ |
| C22 | ○ | ○ | ⊙ | ○ |
| Comparative Example | | | | |
| HC1 | X | Δ | ○ | ○ |
| HC2 | X | Δ | ○ | ○ |
| HC3 | X | Δ | ○ | ○ |
| HC4 | X | Δ | ○ | ○ |

As is seen from the results in Table 2, it is found that the photoacid generator of the invention have an excellent ability to cure a cationically polymerizable compound with ultraviolet light at 365 nm or more (high photosensitivity) as compared with the comparative photoacid generator.

[Evaluation of Chemically Amplified Positive Photoresist Compositions]

<Preparation of Samples for Evaluation>

As shown in Table 3, 1 part by weight of the ingredient (A) (photoacid generator), 40 parts by weight of the resin ingredient (B) (the resin represented by chemical formula (Resin-1) described below), and 60 parts by weight of the resin ingredient (C) (a novolac resin obtained by addition-condensation of m-cresol and p-cresol in the presence of formaldehyde and an acid catalyst) were uniformly dissolved in solvent-2 (propylene glycol monomethyl ether acetate). The solution was filtered through a membrane filter with a pore size of 1 μm, so that a positive photoresist composition with solids content of 40% by weight (each of Examples P1 to P28) was prepared.

A comparative chemically amplified positive photoresist composition (each of Comparative Examples HP1 to HP7) was also prepared in the same manner using the amounts formulated shown in Table 3.

TABLE 3

| Example | Example of the corresponding photoacid generator (A) | Amount of photoacid generator (A) formulated | Resin ingredient (B) | Resin ingredient (C) | Solvent-2 |
| --- | --- | --- | --- | --- | --- |
| P1 | Example 1 | 1 | 40 | 60 | 151.5 |
| P2 | Example 2 | 1 | 40 | 60 | 151.5 |
| P3 | Example 3 | 1 | 40 | 60 | 151.5 |
| P4 | Example 5 | 1 | 40 | 60 | 151.5 |
| P5 | Example 7 | 1 | 40 | 60 | 151.5 |
| P6 | Example 8 | 1 | 40 | 60 | 151.5 |
| P7 | Example 9 | 1 | 40 | 60 | 151.5 |
| P8 | Example 10 | 1 | 40 | 60 | 151.5 |
| P9 | Example 11 | 1 | 40 | 60 | 151.5 |
| P10 | Example 12 | 1 | 40 | 60 | 151.5 |
| P11 | Example 13 | 1 | 40 | 60 | 151.5 |
| P12 | Example 15 | 1 | 40 | 60 | 151.5 |
| P13 | Example 17 | 1 | 40 | 60 | 151.5 |
| P14 | Example 18 | 1 | 40 | 60 | 151.5 |
| P15 | Example 19 | 1 | 40 | 60 | 151.5 |
| P16 | Example 20 | 1 | 40 | 60 | 151.5 |
| P17 | Example 21 | 1 | 40 | 60 | 151.5 |
| P18 | Example 22 | 1 | 40 | 60 | 151.5 |
| P19 | Example 23 | 1 | 40 | 60 | 151.5 |
| P20 | Example 24 | 1 | 40 | 60 | 151.5 |
| P21 | Example 25 | 1 | 40 | 60 | 151.5 |
| P22 | Example 26 | 1 | 40 | 60 | 151.5 |
| P23 | Example 27 | 1 | 40 | 60 | 151.5 |
| P24 | Example 28 | 1 | 40 | 60 | 151.5 |
| P25 | Example 29 | 1 | 40 | 60 | 151.5 |
| P26 | Example 30 | 1 | 40 | 60 | 151.5 |
| P27 | Example 31 | 1 | 40 | 60 | 151.5 |
| P28 | Example 32 | 1 | 40 | 60 | 151.5 |
| Comparative Example | | | | | |
| HP1 | C. Example 1 | 1 | 40 | 60 | 151.5 |
| HP2 | C. Example 2 | 1 | 40 | 60 | 151.5 |
| HP3 | C. Example 5 | 1 | 40 | 60 | 151.5 |
| HP4 | C. Example 6 | 1 | 40 | 60 | 151.5 |
| HP5 | Ref-1 | 1 | 40 | 60 | 151.5 |
| HP6 | Ref-2 | 1 | 40 | 60 | 151.5 |
| HP7 | Ref-3 | 1 | 40 | 60 | 151.5 |

[Chemical Formula 47]

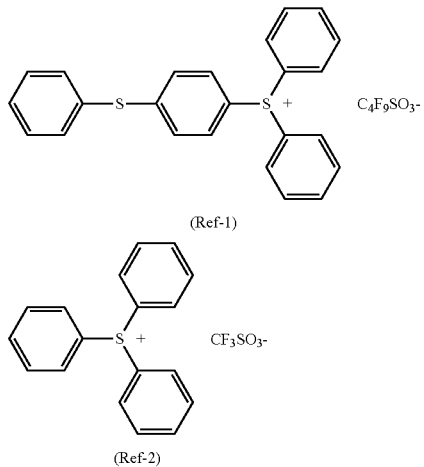

(Ref-1)

(Ref-2)

TABLE 3-continued

| Example | Example of the corresponding photoacid generator (A) | Amount of photoacid generator (A) formulated | Resin ingredient (B) | Resin ingredient (C) | Solvent-2 |
|---|---|---|---|---|---|

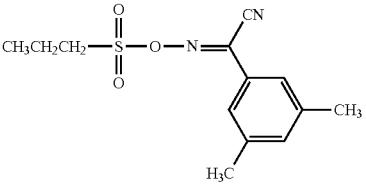

(Ref-3)

[Chemical Formula 48]

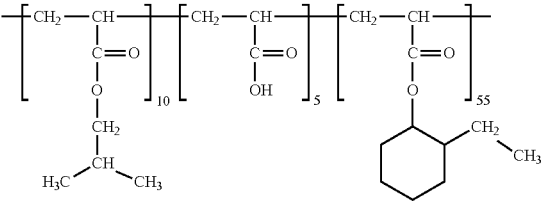

(Resin-1)

<Sensitivity Evaluation>

The positive resist composition prepared in each of Examples P1 to P28 and Comparative Examples HP1 to HP7 described above was applied to a silicon wafer substrate by spin coating and then dried so that a photoresist layer with a thickness of about 20 μm was obtained. The resist layer was prebaked on a hot plate at 130° C. for 6 minutes. After the prebaking, pattern exposure (i-line) was performed using TME-150RSC (manufactured by TOPCON CORPORATION), and post-exposure baking (PEB) was performed with a hot plate at 75° C. for 5 minutes. Subsequently, a developing treatment was performed for 5 minutes by an immersion method using an aqueous solution of 2.38% by weight tetramethylammonium hydroxide. The layer was washed with flowing water, and nitrogen was blown, so that a 10 μm line and space (L & S) pattern was obtained. In addition, measurement was performed to determine the minimum exposure dose below which no residual pattern was observed, namely, the minimum essential exposure dose (corresponding to the sensitivity) necessary for the formation of the resist pattern.

<Evaluation of Storage Stability>

Using the chemically amplified positive photoresist composition prepared as described above, the photosensitivity (sensitivity) immediately after the preparation and after one-month storage at 40° C. was evaluated as described above, and the storage stability was evaluated according to the following criteria.

◯: After one-month storage at 40° C., the sensitivity is changed by less than 5% from that immediately after the preparation.

x: After one-month storage at 40° C., the sensitivity is changed by 5% or more from that immediately after the preparation.

<Evaluation of Pattern Shape>

The cross-sectional shape of the 10 μm L & S pattern formed on the silicon wafer substrate by the above process was measured for the lower side size La and the upper side size Lb using a scanning electron microscope, and the pattern shape was evaluated according to the criteria below. The results are shown in Table 4.

⊙: 0.90 Lb/La 1
◯: 0.85 Lb/La<0.90
x: Lb/La<0.85

TABLE 4

| Example | Example of the corresponding photoacid generator (A) | Minimum essential exposure dose (mJ/cm²) | Storage stability | Pattern shape |
|---|---|---|---|---|
| P1 | Example 1 | 180 | ◯ | ◯ |
| P2 | Example 2 | 160 | ◯ | ◯ |
| P3 | Example 3 | 160 | ◯ | ◯ |
| P4 | Example 5 | 160 | ◯ | ◯ |
| P5 | Example 7 | 170 | ◯ | ◯ |
| P6 | Example 8 | 170 | ◯ | ◯ |
| P7 | Example 9 | 180 | ◯ | ◯ |
| P8 | Example 10 | 180 | ◯ | ◯ |
| P9 | Example 11 | 180 | ◯ | ◯ |
| P10 | Example 12 | 160 | ◯ | ◯ |
| P11 | Example 13 | 160 | ◯ | ◯ |
| P12 | Example 15 | 160 | ◯ | ◯ |
| P13 | Example 17 | 170 | ◯ | ◯ |
| P14 | Example 18 | 170 | ◯ | ◯ |
| P15 | Example 19 | 180 | ◯ | ◯ |
| P16 | Example 20 | 180 | ◯ | ◯ |
| P17 | Example 21 | 160 | ◯ | ◯ |
| P18 | Example 22 | 160 | ◯ | ◯ |
| P19 | Example 23 | 160 | ◯ | ◯ |
| P20 | Example 24 | 160 | ◯ | ◯ |
| P21 | Example 25 | 160 | ◯ | ◯ |
| P22 | Example 26 | 160 | ◯ | ◯ |
| P23 | Example 27 | 160 | ◯ | ◯ |
| P24 | Example 28 | 160 | ◯ | ◯ |
| P25 | Example 29 | 160 | ◯ | ◯ |
| P26 | Example 30 | 160 | ◯ | ◯ |
| P27 | Example 31 | 160 | ◯ | ◯ |
| P28 | Example 32 | 160 | ◯ | ◯ |
| Comparative Example | | | | |
| HP1 | C.Example 1 | 290 | ◯ | ◯ |
| HP2 | C.Example 2 | 290 | ◯ | ◯ |
| HP3 | C.Example 5 | 300 | ◯ | ◯ |

TABLE 4-continued

| Example | Example of the corresponding photoacid generator (A) | Minimum essential exposure dose (mJ/cm$^2$) | Storage stability | Pattern shape |
|---|---|---|---|---|
| HP4 | C.Example 6 | 310 | ○ | ○ |
| HP5 | Ref-1 | 1100 | ○ | ○ |
| HP6 | Ref-2 | 5000 or more | —* | —* |
| HP7 | Ref-3 | 450 | X | ○ |

*Since the minimum essential exposure dose cannot be determined, it is not possible to evaluate the storage stability.

As shown in Table 4, it is found that the chemically amplified positive photoresist composition of each of Examples P1 to P28 has higher sensitivity than the composition produced with a conventional photoacid generator as in each of Comparative Examples HP1 to HP7. The composition of the invention has excellent storage stability, and provides a better pattern shape.

[Evaluation of Chemically Amplified Negative Photoresist Compositions]

<Preparation of Samples for Evaluation>

As shown in Table 5, 1 part by weight of the ingredient (E) (photoacid generator), 100 parts by weight of the phenolic resin ingredient (F) (a copolymer (Mw=10,000) of p-hydroxystyrene/styrene=80/20 (in molar ratio)), 20 parts by weight of the crosslinking agent ingredient (G) (hexamethoxymethylmelamine (trade name: "NIKALAC MW-390", manufactured by Sanwa Chemical Co., Ltd.), 10 parts by weight of the crosslinked fine particles ingredient (H) (a copolymer comprising butadiene/acrylonitrile/hydroxybutyl methacrylate/methacrylic acid/divinylbenzene=64/20/8/6/2 (% by weight) (average particle size=65 nm, Tg=−38° C.)), and 5 parts by weight of the adhesion auxiliary agent ingredient (I) (γ-glycidoxypropyltrimethoxysilane (trade name: "S510", manufactured by CHISSO CORPORATION)) were uniformly dissolved in 145 parts by weight of solvent-3 (ethyl lactate), so that the chemically amplified negative photoresist composition of the invention (each of Examples N1 to N28) was prepared.

A comparative chemically amplified negative photoresist composition (each of Comparative Examples HN1 to HN7) was also prepared in the same manner using the amounts formulated shown in Table 5.

TABLE 5

| Example | Example of the corresponding photoacid generator (E) | Amount of photoacid generator (E) formulated | Resin ingredient (F) | Resin ingredient (G) | Crosslinked fine particles ingredient (H) | Adhesion auxiliary agent (I) | Solvent-3 |
|---|---|---|---|---|---|---|---|
| N1 | Example 1 | 1 | 100 | 20 | 10 | 5 | 145 |
| N2 | Example 2 | 1 | 100 | 20 | 10 | 5 | 145 |
| N3 | Example 3 | 1 | 100 | 20 | 10 | 5 | 145 |
| N4 | Example 5 | 1 | 100 | 20 | 10 | 5 | 145 |
| N5 | Example 7 | 1 | 100 | 20 | 10 | 5 | 145 |
| N6 | Example 8 | 1 | 100 | 20 | 10 | 5 | 145 |
| N7 | Example 9 | 1 | 100 | 20 | 10 | 5 | 145 |
| N8 | Example 10 | 1 | 100 | 20 | 10 | 5 | 145 |
| N9 | Example 11 | 1 | 100 | 20 | 10 | 5 | 145 |
| N10 | Example 12 | 1 | 100 | 20 | 10 | 5 | 145 |
| N11 | Example 13 | 1 | 100 | 20 | 10 | 5 | 145 |
| N12 | Example 15 | 1 | 100 | 20 | 10 | 5 | 145 |
| N13 | Example 17 | 1 | 100 | 20 | 10 | 5 | 145 |
| N14 | Example 18 | 1 | 100 | 20 | 10 | 5 | 145 |
| N15 | Example 19 | 1 | 100 | 20 | 10 | 5 | 145 |
| N16 | Example 20 | 1 | 100 | 20 | 10 | 5 | 145 |
| N17 | Example 21 | 1 | 100 | 20 | 10 | 5 | 145 |
| N18 | Example 22 | 1 | 100 | 20 | 10 | 5 | 145 |
| N19 | Example 23 | 1 | 100 | 20 | 10 | 5 | 145 |
| N20 | Example 24 | 1 | 100 | 20 | 10 | 5 | 145 |
| N21 | Example 25 | 1 | 100 | 20 | 10 | 5 | 145 |
| N22 | Example 26 | 1 | 100 | 20 | 10 | 5 | 145 |
| N23 | Example 27 | 1 | 100 | 20 | 10 | 5 | 145 |
| N24 | Example 28 | 1 | 100 | 20 | 10 | 5 | 145 |
| N25 | Example 29 | 1 | 100 | 20 | 10 | 5 | 145 |
| N26 | Example 30 | 1 | 100 | 20 | 10 | 5 | 145 |
| N27 | Example 31 | 1 | 100 | 20 | 10 | 5 | 145 |
| N28 | Example 32 | 1 | 100 | 20 | 10 | 5 | 145 |
| C. Example | | | | | | | |
| HN1 | C. Example 1 | 1 | 100 | 20 | 10 | 5 | 145 |
| HN2 | C. Example 2 | 1 | 100 | 20 | 10 | 5 | 145 |
| HN3 | C. Example 5 | 1 | 100 | 20 | 10 | 5 | 145 |
| HN4 | C. Example 6 | 1 | 100 | 20 | 10 | 5 | 145 |
| HN5 | Ref-1 | 1 | 100 | 20 | 10 | 5 | 145 |
| HN6 | Ref-2 | 1 | 100 | 20 | 10 | 5 | 145 |
| HN7 | Ref-3 | 1 | 100 | 20 | 10 | 5 | 145 |

<Sensitivity Evaluation>

Each composition was applied to a silicon wafer substrate by spin coating and then dried by heating with a hot plate at 110° C. for 3 minutes, so that a resin coating film with a thickness of about 20 μm was obtained. Subsequently, pattern exposure (i-line) was performed using TME-150RSC (manufactured by TOPCON CORPORATION), and post-exposure baking (PEB) was performed with a hot plate at 110° C. for 3 minutes. Subsequently, a developing treatment was performed for 2 minutes by an immersion method using an aqueous solution of 2.38% by weight tetramethylammonium hydroxide. The layer was washed with flowing water, and nitrogen was blown, so that a 10 μm line and space pattern was obtained. In addition, measurement was performed to determine the minimum essential exposure dose (corresponding to the sensitivity) necessary for the formation of a pattern with a remaining thickness ratio of 95% or more (which indicates the ratio of the remaining film after the development to that before the development).

<Evaluation of Storage Stability>

Using the chemically amplified negative photoresist composition prepared as described above, the photosensitivity (sensitivity) immediately after the preparation and after one-month storage at 40° C. was evaluated as described above, and the storage stability was evaluated according to the following criteria.
- ○: After one-month storage at 40° C., the sensitivity is changed by less than 5% from that immediately after the preparation.
- x: After one-month storage at 40° C., the sensitivity is changed by 5% or more from that immediately after the preparation.

<Evaluation of Pattern Shape>

The cross-sectional shape of the 20 μm L & S pattern formed on the silicon wafer substrate by the above process was measured for the lower side size La and the upper side size Lb using a scanning electron microscope, and the pattern shape was evaluated according to the criteria below. The results are shown in Table 6.
- ⊙: 0.90 La/Lb 1
- ○: 0.85 La/Lb<0.90
- x: La/Lb<0.85

TABLE 6

| | Example of the corresponding photoacid generator (E) | Minimum essential exposure dose (mJ/cm²) | Storage stability | Pattern shape |
|---|---|---|---|---|
| Example | | | | |
| N1 | Example 1 | 140 | ○ | ○ |
| N2 | Example 2 | 120 | ○ | ○ |
| N3 | Example 3 | 120 | ○ | ○ |
| N4 | Example 5 | 120 | ○ | ○ |
| N5 | Example 7 | 130 | ○ | ○ |
| N6 | Example 8 | 130 | ○ | ○ |
| N7 | Example 9 | 140 | ○ | ○ |
| N8 | Example 10 | 140 | ○ | ○ |
| N9 | Example 11 | 140 | ○ | ○ |
| N10 | Example 12 | 120 | ○ | ○ |
| N11 | Example 13 | 120 | ○ | ○ |
| N12 | Example 15 | 120 | ○ | ○ |
| N13 | Example 17 | 130 | ○ | ○ |
| N14 | Example 18 | 130 | ○ | ○ |
| N15 | Example 19 | 140 | ○ | ○ |
| N16 | Example 20 | 140 | ○ | ○ |
| N17 | Example 21 | 120 | ○ | ○ |
| N18 | Example 22 | 120 | ○ | ○ |
| N19 | Example 23 | 120 | ○ | ○ |
| N20 | Example 24 | 120 | ○ | ○ |
| N21 | Example 25 | 120 | ○ | ○ |
| N22 | Example 26 | 120 | ○ | ○ |
| N23 | Example 27 | 120 | ○ | ○ |
| N24 | Example 28 | 120 | ○ | ○ |
| N25 | Example 29 | 120 | ○ | ○ |
| N26 | Example 30 | 120 | ○ | ○ |
| N27 | Example 31 | 120 | ○ | ○ |
| N28 | Example 32 | 120 | ○ | ○ |

TABLE 6-continued

| | Example of the corresponding photoacid generator (E) | Minimum essential exposure dose (mJ/cm²) | Storage stability | Pattern shape |
|---|---|---|---|---|
| Comparative Example | | | | |
| HN1 | C.Example 1 | 240 | ○ | ○ |
| HN2 | C.Example 2 | 240 | ○ | ○ |
| HN3 | C.Example 5 | 250 | ○ | ○ |
| HN4 | C.Example 6 | 260 | ○ | ○ |
| HN5 | Ref-1 | 850 | ○ | ○ |
| HN6 | Ref-2 | 3000 or more | —* | —* |
| HN7 | Ref-3 | 350 | X | ○ |

*Since the minimum essential exposure dose cannot be determined, it is not possible to evaluate the storage stability.

As shown in Table 6, it is found that the chemically amplified negative photoresist composition of each of Examples N1 to N28 has lower minimum essential exposure dose than the composition in each of Comparative Examples N1 to N4. The photoacid generator of the invention has higher sensitivity, and has excellent storage stability, and provides a better pattern shape than the comparative photoacid generator.

INDUSTRIAL APPLICABILITY

The sulfonium salt of the present invention is suitably used for paints, coating agents, various coating materials (hard coats, anti-fouling coating materials, anti-fogging coating materials, anti-corrosion coating materials, optical fibers and the like), back surface treatment agents for pressure sensitive adhesive tapes, release coating materials of release sheets for pressure sensitive adhesive labels (release papers, release plastic films, release metal foils and the like), printing plates, dental materials (dental formulations and dental composites), ink compositions, inkjet ink compositions, positive resists (for formation of connection terminals and wiring patterns in production of electronic components such as circuit boards, CSP and MEMS elements), resist films, liquid resists and negative resists (permanent film materials of surface protecting films, interlayer dielectric films, planarizing films for semiconductor elements, etc.), resists for MEMS, positive photosensitive materials, negative photosensitive materials, various adhesives (various temporary fixing agents for electronic components, adhesives for HDD, adhesives for pick-up lenses, functional films for FPD (polarizing plates, antireflection films and the like), etc.), holographic resins, FPD materials (color filters, black matrices, partition wall materials, photospacers, ribs, orientation films for liquid crystals, sealing agents for FPD and the like), optical members, molding materials (for building materials, optical components and lenses), casting materials, putty materials, glass fiber impregnating agents, fillers, sealing materials, sealants, photosemiconductor (LED) sealing materials, optical waveguide materials, nano-imprint materials, stereolithography materials, and micro-stereolithography materials.

The invention claimed is:

1. A sulfonium salt represented by formula (1) described below.

[Chemical Formula 1]

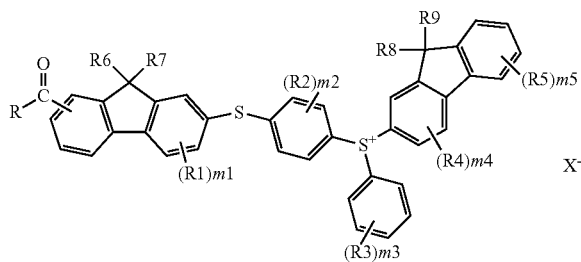

(1)

2. The sulfonium salt according to claim 1, wherein substituents, R1 to R5, each independently represent an alkyl group, or an alkoxy group.

3. The sulfonium salt according to claim 1, wherein R6 to R9 are a methyl group.

4. The sulfonium salt according to claim 1, wherein $m^1$ to $m^5$ are 0.

5. The sulfonium salt according to claim 1, wherein R is a methyl group, or phenyl group.

6. The sulfonium salt according to claim 1, wherein $X^-$ is an anion represented by $MY_a^-$, $(Rf)_bPF_{6-b}^-$, $R^{10}{}_cBy_{4-c}^-$, $R^{10}{}_cGaY_{4-c}^-$, $R^{11}SO_3^-$, $(R^{11}SO_2)_3C^-$, or $(R^{11}SO_2)_2N^-$ (wherein M represents a phosphorus atom, a boron atom, an arsenic atom, or an antimony atom, Y represents a halogen atom, Rf represents an alkyl group, 80% by mole or more of whose hydrogen atoms are substituted with fluorine atoms, P represents a phosphorus atom, F represents a fluorine atom, $R^{10}$ represents a phenyl group, at least one of whose hydrogen atoms is substituted with a halogen atom, a trifluoromethyl group, a nitro group, or a cyano group, B represents a boron atom, Ga represents a gallium atom, $R^{11}$ represents an alkyl group having 1 to 20 carbon atoms, a perfluoroalkyl group having 1 to 20 carbon atoms, or an aryl group having 6 to 20 carbon atoms, a represents an integer of 4 to 6, b represents an integer of 1 to 5, and c represents an integer of 1 to 4).

7. The sulfonium salt according to claim 1, wherein $X^-$ is an anion represented by $SbF_6^-$, $PF_6^-$, $BF_4^-$, $(CF_3CF_2)_3PF_3^-$, $(CF_3CF_2CF_2CF_2)_3PF_3^-$, $(C_6F_5)_4B^-$, $(C_6H_5)(C_6F_5)_3B^-$, $((CF_3)_2C_6H_3)_4B^-$, $(C_6F_5)_4Ga^-$, $((CF_3)_2C_6H_3)_4Ga^-$, trifluoromethanesulfonate anion, nonafluorobutanesulfonate anion, methanesulfonate anion, butanesulfonate anion, camphorsulfonate anion, benzenesulfonate anion, p-toluenesulfonate anion, $(CF_3SO_2)_3C^-$, or $(CF_3SO_2)_2N^-$.

8. A photoacid generator, comprising the sulfonium salt according to claim 1.

9. An energy ray-curable composition, comprising the photoacid generator according to claim 8 and a cationically polymerizable compound.

10. A cured product obtained by curing the energy ray-curable composition according to claim 9.

11. A chemically amplified positive photoresist composition, comprising: an ingredient (A) comprising the photoacid generator according to claim 8; and a resin ingredient (B) increasing its solubility in an alkali under the action of an acid.

12. The chemically amplified positive photoresist composition according to claim 11, wherein the ingredient (B) comprises at least one resin selected from the group consisting of a novolac resin (B1), a polyhydroxystyrene resin (B2), and an acrylic resin (B3).

13. The chemically amplified positive photoresist composition according to claim 11, further comprising an alkali-soluble resin (C) and an acid diffusion controlling agent (D).

14. A method for forming a resist pattern, comprising: a lamination step of laminating, on a support, a photoresist layer with a thickness of 10 to 150 μm comprising the chemically amplified positive photoresist composition according to claim 11 to obtain a photoresist laminate; an exposure step of site-selectively irradiating the photoresist laminate with light or a radiation; and a development step of developing the photoresist laminate after the exposure step to obtain a resist pattern.

15. A chemically amplified negative photoresist composition, comprising: an ingredient (E) comprising the photoacid generator according to claim 8; an ingredient (F) that is an alkali-soluble resin having a phenolic hydroxyl group; and a crosslinking agent ingredient (G).

16. The chemically amplified negative photoresist composition according to claim 15, further comprising a crosslinked fine particles ingredient (H).

17. A cured product obtained by curing the chemically amplified negative photoresist composition according to claim 15.

* * * * *